(12) United States Patent
Huang et al.

(10) Patent No.: US 12,205,681 B1
(45) Date of Patent: Jan. 21, 2025

(54) NUCLIDE IDENTIFICATION METHOD, SYSTEM AND ELECTRONIC DEVICE

(71) Applicant: NATIONAL INSTITUTE OF METROLOGY, CHINA, Beijing (CN)

(72) Inventors: Jianwei Huang, Beijing (CN); Xuan Zhang, Beijing (CN); Linjian Wan, Beijing (CN); Dehong Li, Beijing (CN); Zhijun Yang, Beijing (CN); Chuanfeng Liu, Beijing (CN); Xiaole Zhang, Beijing (CN); Siming Guo, Beijing (CN); Yang Yang, Beijing (CN); Jianbo Cheng, Beijing (CN); Yilun Xu, Beijing (CN)

(73) Assignee: National Institute of Metrology, China, Beijing (CN)

( * ) Notice: Subject to any disclaimer, the term of this patent is extended or adjusted under 35 U.S.C. 154(b) by 0 days.

(21) Appl. No.: 18/760,328

(22) Filed: Jul. 1, 2024

(30) Foreign Application Priority Data

Jan. 25, 2024 (CN) .......................... 202410107288.6

(51) Int. Cl.
*G16C 20/20* (2019.01)

(52) U.S. Cl.
CPC .................................. *G16C 20/20* (2019.02)

(58) Field of Classification Search
CPC ............. G01T 1/36; G16C 20/20; G06N 7/01
See application file for complete search history.

(56) References Cited

U.S. PATENT DOCUMENTS

2010/0030721 A1* 2/2010 Candy ...................... G06N 7/01
706/52
2014/0365173 A1* 12/2014 Lin ........................... G01T 1/36
702/179

* cited by examiner

*Primary Examiner* — Lam S Nguyen
(74) *Attorney, Agent, or Firm* — McHale & Slavin, P.A.

(57) ABSTRACT

A nuclide identification method, a system and an electronic device are provided, which relates to the field of nuclide identification. According to statistical characteristics, a background probability density function and a Compton probability density function in a ROI are determined. An energy Bayesian factor and a time Bayesian factor are determined based on energy and time interval information in a sequence of the nuclear detection events obtained by measurement. By combining the two factors, Compton plateau can be effectively identified and distinguished.

20 Claims, 11 Drawing Sheets

NUCLIDE IDENTIFICATION METHOD, SYSTEM AND ELECTRONIC DEVICE

CROSS-REFERENCE TO RELATED APPLICATION

In accordance with 37 C.F.R. 1.76, a claim of priority is included in an Application Data Sheet filed concurrently herewith. Accordingly, the present invention claims priority to Chinese Patent Application No. 202410107288.6, entitled "NUCLIDE IDENTIFICATION METHOD, SYSTEM AND ELECTRONIC DEVICE", filed Jan. 25, 2024. The contents of the above referenced application is incorporated herein by reference in its entirety.

FIELD OF THE INVENTION

The present disclosure relates to the field of nuclide identification, in particular to a nuclide identification method, a system and an electronic device.

BACKGROUND OF THE INVENTION

At present, the common traditional nuclide identification methods are based on γ-ray spectrum decomposition analysis technology and characteristic full energy peak matching technology. These two technologies mainly include background subtraction, filtering smoothing and peak searching, and both statistically analyze the characteristic γ-ray emitted by radioactive materials by assuming the Gaussian distribution of the peak shape of the full energy peak and by matching the peak position, thus realizing the qualitative and quantitative determination of radioactive materials. However, these methods need to collect enough photons to reduce the statistical fluctuation of characteristic peaks, so that there are certain requirements for detection time and characteristic γ-ray emission intensity. However, in special security inspection scenes such as ports, airports and borders, there is a large number of people and goods, and the detection target can be measured only for a short time (in seconds). At the same time, the detection target is in motion relative to the detector during the security inspection, which will further affect the number of photons collected by the detector. In addition, radioactive materials are usually placed in well-shielded tanks or containers in these scenes, which causes the distortion of γ-spectrum and reduction in counting rate, which in turn affects the rapid and accurate identification of nuclides by additional influence from environmental background and Compton scattering, and further increases the difficulty of processing γ radiation signals. To sum up, in the special security inspection scenes such as ports, airports and borders, the peak searching-nuclide matching identification method based on a Gaussian model becomes difficult and inaccurate in the process of analyzing γ-spectrum, and the prominent contradiction is reflected in the contradiction between identification speed and accuracy. Although the use of fixed large-volume detectors can alleviate this contradiction to some extent, its high price and large size are the main factors limiting its widespread application.

In addition, at present, the new nuclide identification methods based on full-spectrum analysis mainly include a sequential Bayesian method, a fuzzy mathematical method, a neural network method and a deconvolution method. These methods not only use characteristic full energy peaks as useful information, but also incorporate information such as a branching ratio, a half-life period and an γ spectrum shape into the analysis information to reduce the uncertainty of nuclide identification and improve the detection efficiency under the condition of a low counting rate. The sequential Bayesian nuclide identification method has the advantages of a high identification lower limit and a fast identification speed. The fuzzy mathematical nuclide identification method can still perform accurate identification in a complex environment. The neural network nuclide identification method can simulate any function, and can use the full-spectrum information of radionuclides for analysis, and can quickly and accurately identify nuclides without complicated operations such as smoothing, peak searching and peak fitting.

In view of the characteristics that measurement is non-static, detection time is short and the detected signal is weak in the detection of illegal transportation of radioactive materials in special scenes such as airports, ports and nuclear radiation emergency, new requirements are put forward in measurement technology.

1. The measurable time is short, usually in the range of sub-seconds to more than ten seconds.
2. The obtained information is rich, particularly it is necessary to determine not only the energy of γ rays, but also the information such as the types, intensities and dose of corresponding radionuclides.
3. The reliability of data is high. At a high level of confidence, the requirement of identification efficiency and accuracy is high, and the false alarm rate and the missed alarm rate should be as low as possible.

Traditionally, the characteristic full energy peak matching technology of γ-spectrum is generally used to analyze indicators such as radionuclides and dose. This analysis method usually needs to collect enough photons for identification, that is, it needs to be based on a large number of γ ray measurement cases and long-term measurement to reduce statistical fluctuation and ensure the necessary measurement representativeness and accuracy. In the radiation detection process recommended by the International Atomic Energy Agency (IAEA), there are mainly three categories based on this method: a fixed entrance radiation monitor system, a handheld/portable γ spectrometer and a laboratory high-resolution γ spectrometer. The newly developed fixed large-volume sodium iodide (NaI(Tl)) detector and high-purity germanium (HPGe) detector can accurately identify the types of radionuclides, but the system is very expensive, poor in portability and unable to be deployed quickly. The portable γ-ray spectrometer mainly includes a scintillator γ-ray spectrometer and a semiconductor γ-ray spectrometer. Such detector usually has low detection efficiency and needs long-term measurement to collect enough photons to reduce the statistical fluctuation of counting. The laboratory high-resolution γ spectrometer is mainly a HPGe γ spectrometer cooled by liquid nitrogen. The system is poor in universality, unable to be deployed quickly and is expensive. To sum up, it is difficult to realize the rapid measurement and identification of low-level nuclides in a short time by using the traditional method, that is, a nuclide identification method based on retrieval from the nuclide database and matching of characteristic full energy peaks in the γ-spectrum. On the one hand, such method cannot meet the identification requirements of various nuclides in the complex environment. On the other hand, it is difficult to realize rapid nuclide identification because of the long forming time of characteristic full energy peaks at the peak position in the γ-spectrum. At the same time, the traditional nuclide identification method based on γ-spectrum decomposition analysis and characteristic peak matching is prone to missed alarm events when the net counting rate of full energy peaks is not enough.

In addition, at present, the new nuclide identification methods based on full spectrum analysis mainly include a sequential Bayesian method based on Bayesian theory and sequential probability ratio test (SPRT), a fuzzy mathematical method, a neural network method and a deconvolution method, etc. When adapting to different γ-spectrometers, these methods will have some shortcomings in the universality in certain aspects such as the degree of influence from background and Compton plateau, the false alarm rate, the missed alarm rate and the amount of calculation required. The fuzzy mathematical method, the neural network method and the deconvolution method are based on full spectrum analysis, which require a large number of particles and long measurement time. At the same time, the neural network method and the deconvolution method need a large amount of calculation, so that they are not suitable for real-time online analysis.

The sequential Bayesian nuclide identification method based on the Bayesian theory and SPRT uses three characteristics of the half-life period of the radionuclides, the characteristic γ-ray energy and the branch ratio, selects the appropriate prior function and confidence, updates the decision function by using SPRT, and makes statistical inference on the hypothesis test. However, this method needs to preset some parameters that are related to the samples and should be unknown in the actual measurement process, which will significantly limit the universality of this method. For example, due to preset the time interval parameter term in the test model, this method will have a high false alarm rate at Compton plateau generated by high-energy rays in the low-energy region of interest. In addition, this method uses a Gaussian model for the distribution of background, which does not conform to the actual situation. This leads to some limitations in the application of the existing sequential Bayesian method.

SUMMARY OF THE INVENTION

In order to solve the above problems in the traditional technology, the present disclosure provides a nuclide identification method, a system and an electronic device.

In order to achieve the above objectives, the present disclosure provides the following solutions.

A nuclide identification method is provided, including:
acquiring time-energy information of a ray, and determining whether the ray belongs to one of Region of Interests (ROIs) based on energy information in the time-energy information of the ray;
describing a sequence of all nuclear detection events in the ROI when the ray belongs to the one of the ROIs;
determining an energy Bayesian factor based on energy information in the described sequence of all the nuclear detection events;
determining an energy decision function based on the energy Bayesian factor;
determining a time interval in the ROI based on time information in the described sequence of all the nuclear detection events;
determining a time Bayesian factor based on the time interval;
determining a time decision function based on the time Bayesian factor;
combining the energy decision function and the time decision function to obtain a joint decision function of the ROI;
retrieving a potential nuclide corresponding to the ROI based on a characteristic γ ray corresponding to the ROT, and combining joint decision functions of respective ROIs corresponding to the retrieved nuclide to obtain a nuclide joint decision function; and
determining and identifying the retrieved nuclide based on the nuclide joint decision function.

According to the specific embodiment of the present disclosure, the present disclosure provides the following technical effects.

Based on a Bayesian factor and a sequential posterior probability, the present disclosure significantly improves the universality of the method by setting a range of a time interval on a decision function instead of directly giving a predefined time interval parameter. According to statistical characteristics, a background probability density function and a Compton probability density function in a ROI are determined. An energy Bayesian factor and a time Bayesian factor are determined based on energy and time interval information in a sequence of the nuclear detection events obtained by measurement. By combining the two factors, the sequence of the nuclear detection events can effectively identify and distinguish Compton plateau. Under the same identification conditions and the same confidence level, the nuclide identification method according to the present disclosure can effectively identify the existence and types of radionuclides faster than an energy spectrum decomposition analysis-characteristic peak matching method. Compared with the fuzzy mathematical and neural network nuclide identification methods, the nuclide identification method provided by the present disclosure is more universal.

In addition, compared with the existing sequential nuclide identification method based on the Bayesian theory and SPRT, the nuclide identification method provided by the present disclosure can significantly reduce the false alarm rate and the missed alarm rate, and can effectively identify Compton contribution from high-energy rays appearing in the low-energy ROI.

Further, the present disclosure provides a nuclide identification system, wherein the system is used to implement the nuclide identification method described above; wherein the system includes:
a ray belonging region determining module, configured to acquire time-energy information of a ray, and determine whether the ray belongs to one of Region of Interests (ROIs) based on energy information in the time-energy information of the ray;
a nuclear detection event sequence description module, configured to describe a sequence of all nuclear detection events in the ROI when the ray belongs to the one of the ROIs;
an energy Bayesian factor determining module, configured to determine an energy Bayesian factor based on energy information in the described sequence of all the nuclear detection events;
an energy decision function determining module, configured to determine an energy decision function based on the energy Bayesian factor;
an ROI time interval determining module, configured to determine a time interval in the ROI based on time information in the described sequence of all the nuclear detection events;

- a time Bayesian factor determining module, configured to determine a time Bayesian factor based on the time interval;
- a time decision function determining module, configured to determine a time decision function based on the time Bayesian factor;
- a decision function combining module, configured to combine the energy decision function and the time decision function to obtain a joint decision function of the ROI;
- a nuclide joint decision function determining module, configured to retrieve a potential nuclide corresponding to the ROI based on a characteristic γ-ray corresponding to the ROI, and combine joint decision functions of respective ROIs corresponding to the retrieved nuclide to obtain a nuclide joint decision function; and
- a nuclide identification module, configured to determine and identify the retrieved nuclide based on the nuclide joint decision function.

Still further, the present disclosure further provides an electronic device, including:

- a memory in which a computer program is stored; and
- a processor connected with the memory, which is configured to call and execute the computer program to implement the nuclide identification method described above.

Since the technical effects achieved by the system and the electronic device according to the present disclosure are the same as those achieved by the nuclide identification method provided above, the technical effects will not be described in detail herein.

BRIEF DESCRIPTION OF THE DRAWINGS

In order to illustrate embodiments of the present disclosure or the technical solutions in the prior art more clearly, the drawings used in the embodiments will be briefly described below. Apparently, the drawings described below are only some embodiments of the present disclosure. For those skilled in the art, other drawings can be obtained according to these drawings without creative efforts.

DETAILED DESCRIPTION OF THE INVENTION

The technical solutions in the embodiments of the present disclosure will be clearly and completely described below in conjunction with the drawings in the embodiments of the present disclosure. Apparently, the described embodiments are merely a part of the embodiments of the present disclosure, rather than all of the embodiments. All other embodiments obtained by those skilled in the art based on the embodiment of the present disclosure without creative efforts shall fall within the scope of the present disclosure.

The present disclosure aims to provide a nuclide identification method, a system and an electronic device, which can well distinguish Compton plateau, effectively identify the existence and types of radionuclides faster and have more universality.

In order to make the above objectives, features and advantages of the present disclosure clearer and more comprehensible, the present disclosure will be described in further detail below in conjunction with the drawings and specific implementations.

Figure 1:
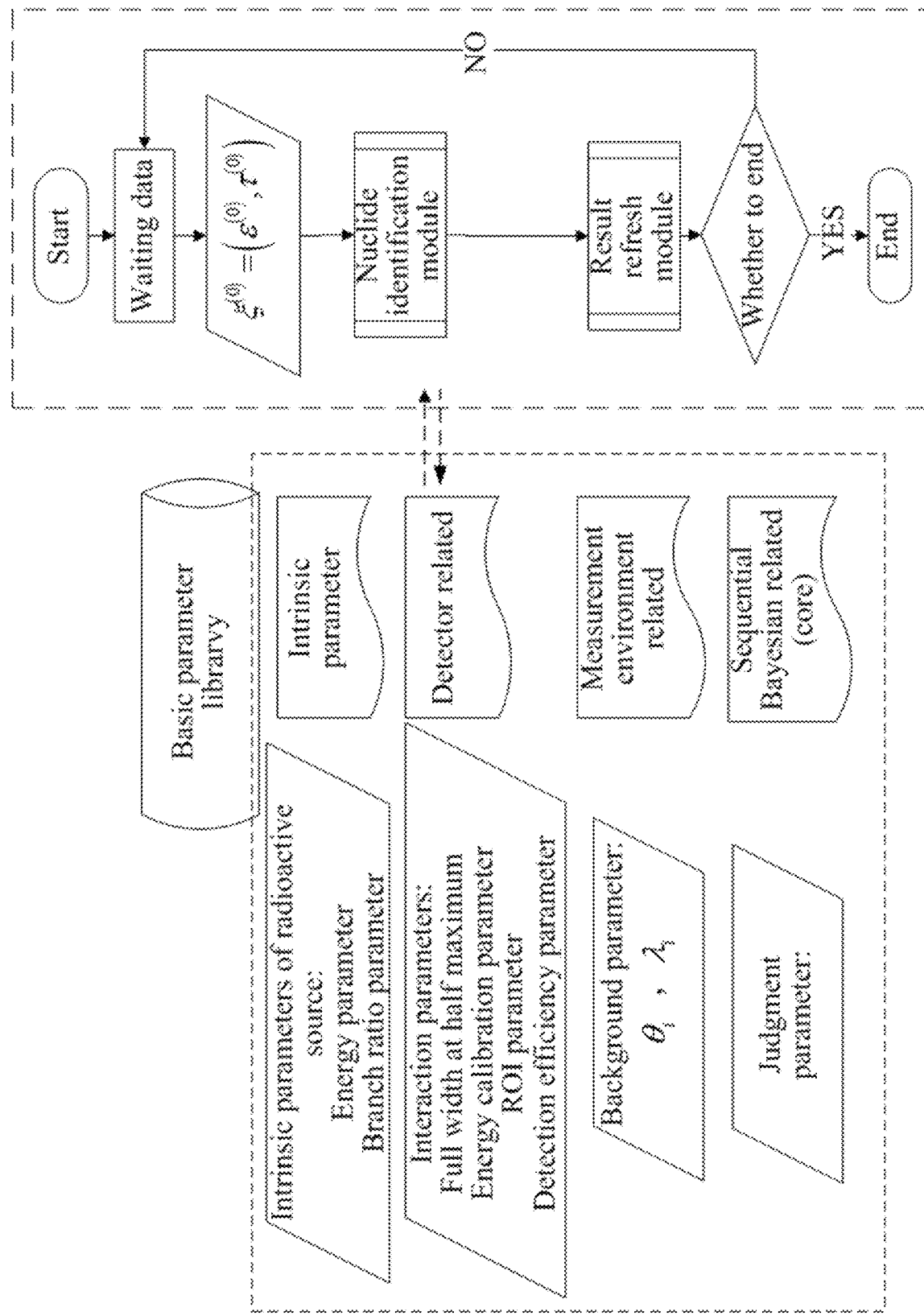
FIG. 1 is an overall flow chart of a nuclide identification method according to the present disclosure.
Figure 2A:
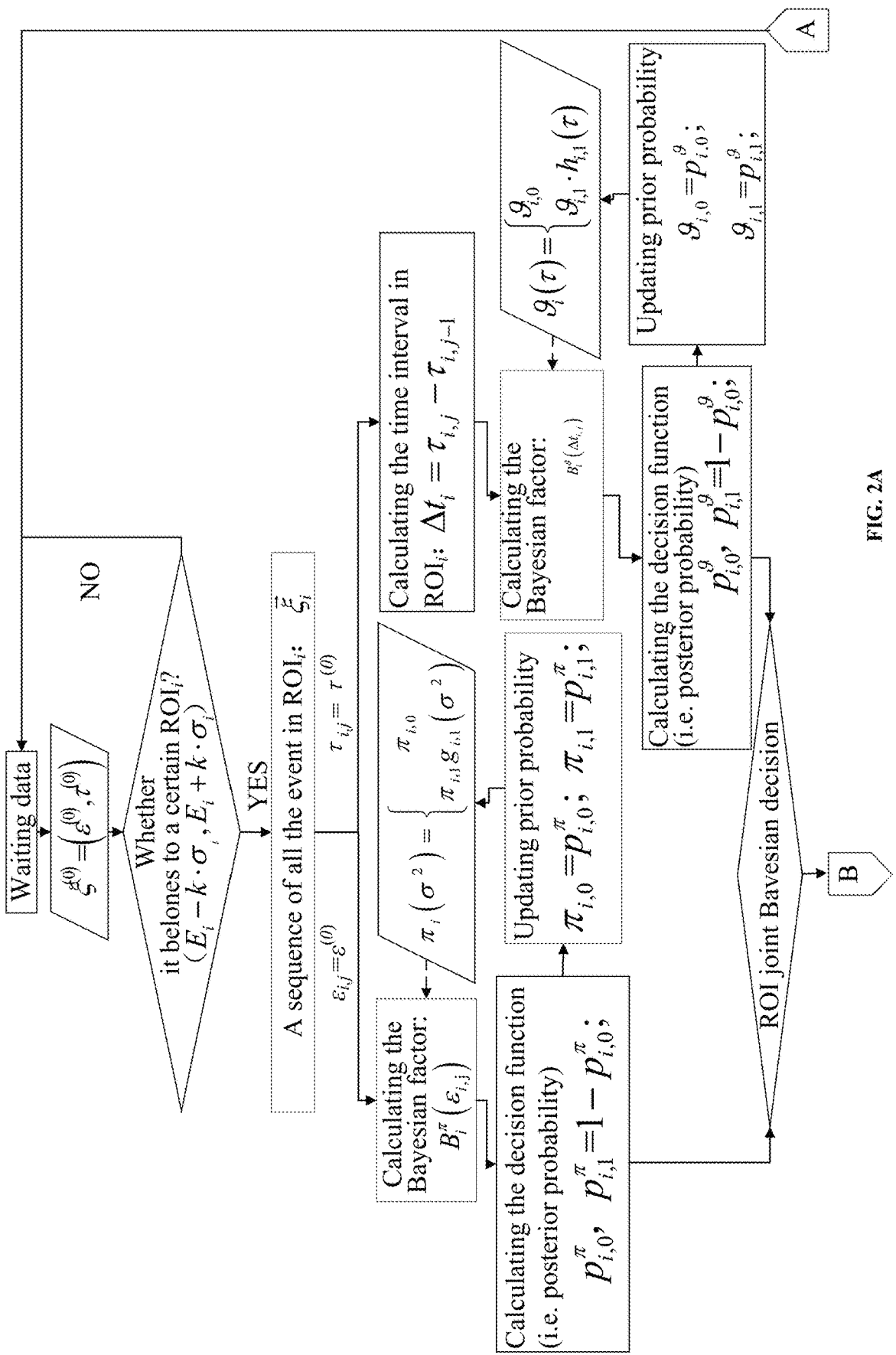
FIGS. 2A and 2B together form an implementation flow chart of the nuclide identification method according to the present disclosure.
Figure 2B:
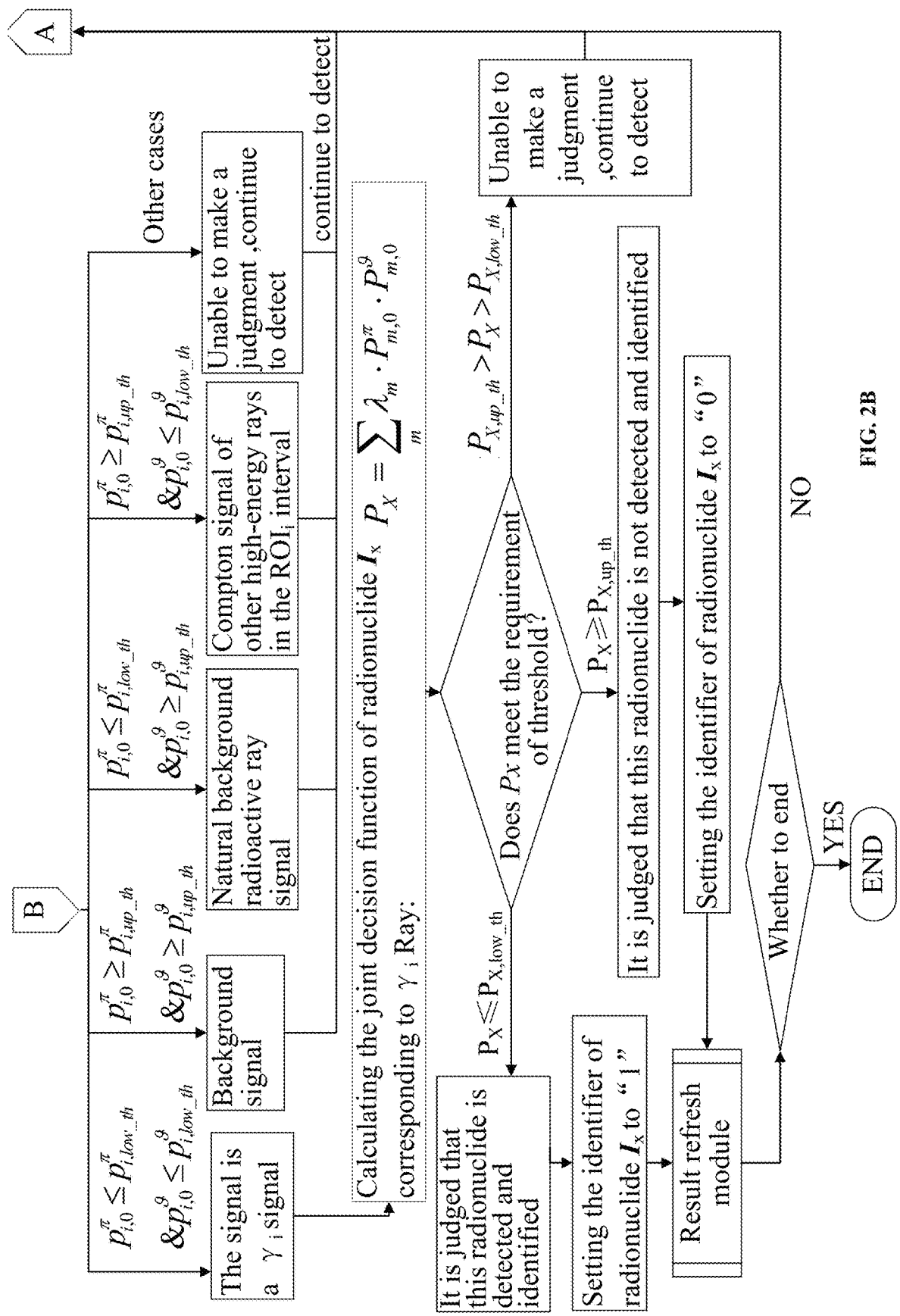

When γ rays are incident on the sensitive volume of a γ spectrometer measurement system, the measurement system outputs the energy and time data pair (ε, t) of the rays to an upper computer. The upper computer calculates the decision function and completes statistical inference based on the energy and time data pair (ε, t) of the incident rays according to the nuclide rapid identification algorithm, and makes effective inference on the existence and types of radionuclides. Based on this, as shown in FIGS. 1 and 2A-2B, the nuclide identification method according to the present disclosure includes the following steps.

Step 1: Region of Interest (ROI) Identification

When a detector detects a ray, time-energy information $\xi^{(0)}=(\varepsilon^{(0)},\tau^{(0)})$ of the ray is outputted, and it is determined whether the ray belongs to a certain ROI according to the energy information $\varepsilon^{(0)}$. If not, the ray is discarded. If the ray belongs to a certain ROI region, such as $ROI_i$ region, a sequence $\vec{\xi}_i$ of all nuclear detection events in this $ROI_i$ can be described as follows:

$$\vec{\xi}_i = \{\xi_{i,j}, \xi_{i,j-1}, \ldots\}$$

$$\xi_{i,j} = (\varepsilon_{i,j}, \tau_{i,j}) = \xi^{(0)}$$

$$\varepsilon_{i,j} = \varepsilon^{(0)}, \tau_{i,j} = \tau^{(0)}$$

where denotes $\xi_{i,j}$ the time and energy information of the j-th ray in the $ROI_i$, where $ROI_i$ represents the i-th region of interest, which is expressed as:

$$ROI_i = (E_i - k \cdot \sigma_i, E_i + k \cdot \sigma_i)$$

where $E_i$ denotes the energy of the characteristic γ ray corresponding to the i-th ROI, k is a coverage factor, and $\sigma_i$ is a standard deviation of the full energy peak of the characteristic γ ray corresponding to the i-th ROI.

Step 2: Calculation of the Energy Bayesian Factor $$B_i^\pi(\varepsilon_{i,j}) = \frac{f_{i,0}(\varepsilon_{i,j}|\sigma_{i,0}^2)}{\int g_{i,1}(\sigma_{i,1}^2) f_{i,1}(\varepsilon_{i,j}|\sigma_{i,1}^2) d(\sigma_{i,1}^2)}$$

where $B_i^\pi(\varepsilon_{i,j})$ is the j-th energy Bayesian factor of the ROI$_i$ calculated according to the energy information of the current ray, $f_{i,0}(\varepsilon_{i,j}|\sigma_{i,0}^2)$ and $f_{i,1}(\varepsilon_{i,j}|\sigma_{i,1}^2)$ are the energy probability density functions under the energy null hypothesis $H_0$ (there is no full energy peak) and the energy alternative hypothesis $H_1$ (there is full energy peak), respectively, $\sigma_{i,0}^2$ and $\sigma_{i,1}^2$ are the standard variances of the energy under $H_0$ and $H_1$, respectively, and $g_{i,1}(\sigma_{i,1}^2)$ is the prior probability under $H_1$. Moreover:

$$\begin{cases} H_0: f_{i,0}(\varepsilon_{i,j}|\sigma_{i,0}^2) = k_i \cdot (\varepsilon_{i,j} - E_i) + 1/\Delta_{E_i}, \ \sigma_{i,0}^2 = \Delta_{E_i}^2/12 \\ H_1: f_{i,1}(\varepsilon_{i,j}|\sigma_{i,1}^2) = p \dfrac{A}{\sqrt{2 \cdot \pi \cdot \sigma_{i,1}^2}} \cdot e^{-\frac{(\varepsilon_{i,j} - E_i)^2}{2\sigma_{i,1}^2}} + (1-p) \cdot f_{i,0}(\varepsilon_{i,j}|\sigma_{i,0}^2), \\ \Delta_{E_i}^2/C_k < \sigma_{i,1}^2 < \Delta_{E_i}^2/12 \end{cases}$$

$$\pi_i(\sigma^2) = \begin{cases} \pi_{i,0}, & \sigma^2 = \Delta_{E_i}^2/12 \\ \pi_{i,1}g_{i,1}(\sigma^2), & \Delta_{E_i}^2/C_k < \sigma^2 < \Delta_{E_i}^2/12 \end{cases}$$

where $\Delta_{E_i} = 2 \cdot k \cdot \sigma_{i,1}$ is an energy width of the ROI$_i$, $\pi_i(\sigma^2)$ is an energy prior probability density function of the ROI$_i$, and $\pi_{i,0}$ and $\pi_{i,1}$ are the energy prior probability under $H_0$ and $H_1$, respectively.

Step 3: Calculation of the Energy Decision Function $$p_{i,0}^\pi = \left[1 + \frac{1 - \pi_{i,0}}{\pi_{i,0}} \frac{1}{B_i^\pi(\varepsilon_{i,j})}\right]^{-1};$$

$$p_{i,1}^\pi = 1 - p_{i,0}^\pi;$$

where $p_{i,0}^\pi$ and $p_{i,1}^\pi$ are the energy posterior probability of the ROI$_i$ calculated according to energy of the current ray under $H_0$ and $H_1$, respectively, which are also the decision functions of γ-ray decision making.

Step 4: Updating of the Energy Prior Probability $$\pi_{i,0} = p_{i,0}^\pi;$$

$$\pi_{i,1} = p_{i,1}^\pi;$$

Step 5: Calculation of the Time Interval in the ROI$_i$

The sequence $\vec{\xi}_i$ of the nuclear detection events in the ROI$_i$ in Step 1 is used to calculate the time interval in the ROI$_i$, which is:

$$\Delta t_{i,j} = \tau_{i,j} - \tau_{i,j-1}$$

where $\tau_{i,j}$ is the measurement moment of the current ray, and $\tau_{i,j-1}$ is the measurement moment of the previous ray in the ROI$_i$.

Step 6: Calculation of the Time Bayesian Factor in the ROI$_i$ $$B_i^\vartheta(\Delta t_{i,j}) = \frac{g_{i,0}(\Delta t_{i,j}|\tau_{i,0})}{\int h_{i,1}(\tau_{i,1}) \cdot g_{i,1}(\Delta t_{i,j}|\tau_{i,1}) d\tau_{i,1}}$$

where $B_{\Delta t}^\vartheta(\Delta t_{i,j})$ is a time Bayesian factor, $g_{i,0}(\Delta t_{i,j}|\tau_{i,0})$ is a time interval probability density function under the time null hypothesis $M_0$ (there are no radionuclides), $g_{i,1}(\Delta t_{i,j}|\tau_{i,1})$ is a time interval probability density function under the time alternative hypothesis $M_1$ (there are radionuclides), $\tau_{i,0}$ is the mathematic expectation of the time interval under the time null hypothesis $M_0$, $\tau_{i,1}$ is a mathematic expectation of the time interval under the time alternative hypothesis $M_1$, $\Delta t_{i,j}$ is a time interval, and $h_{i,1}(\tau_{i,1})$ is the probability density function under the time alternative hypothesis $M_1$. Moreover:

$$\begin{cases} M_0: g_0(\Delta t|\tau_0) = \dfrac{1}{\tau_0} \cdot e^{-\frac{\Delta t}{\tau_0}}, \ \tau_0 = \tau_{bkg} = \dfrac{1}{\dot{n}_{bkg}} \\ M_1: g_1(\Delta t|\tau_1) = \dfrac{1}{\tau_1} \cdot e^{-\frac{\Delta t}{\tau_1}}, \ \tau_1 \in (\tau_{min}, \tau_{bkg}) \end{cases}$$

$$\vartheta(\tau) = \begin{cases} \vartheta_0, & \tau = \tau_{bkg} \\ \vartheta_1 \cdot h_1(\tau), & \tau \in (\tau_{min}, \tau_{bkg}) \end{cases}$$

where $g_0(\Delta t_{i,j}|\tau_0)$ and $g_1(\Delta t_{i,j}|\tau_1)$ are the time interval probability density function under the time null hypothesis $M_0$ (there are no radionuclides) and the time alternative hypothesis $M_1$ (there are radionuclides), respectively, $\tau_0$ and $\tau_1$ the mathematic expectations of the time interval under $M_0$ and $M_1$, respectively, $h_1(\tau_1)$ is a probability density function under $M_1$, $$h_1(\tau) \propto \frac{1}{\tau}, \dot{n}_{bkg}$$

and $\tau_{bkg}$ are the count rate and the mean of the time interval under the background condition, respectively, which are reciprocal to each other, and $\tau_{min}$ is a parameter determining a lower limit $\eta_{min}$ of detection sensitivity under $M_1$. The lower limit $\eta_{min}$ of detection sensitivity is defined as the minimum signal-to-noise ratio η that can make effective determination under active conditions and meet certain detection performance requirements, and the signal-to-noise ratio is the ratio of the full-spectrum net count rate to the background counting rate. $\vartheta(\tau)$ is the prior probability density function of the full-spectrum time interval. $\vartheta_0$ and $\vartheta_1$ are the prior probabilities under $M_0$ and $M_1$, respectively, in which $\vartheta_0 + \vartheta_1 = 1$.

Step 7: Calculation of the Time Decision Function $$p_{i,0}^\vartheta = \left[1 + \frac{1 - \vartheta_{i,0}}{\vartheta_{i,0}} \frac{1}{B_i^\vartheta(\Delta t_{i,j})}\right]^{-1}$$

$$p_{i,j}^\vartheta = 1 - p_{i,0}^\vartheta;$$

where $p_{i,0}^\vartheta$ and $p_{i,1}^\vartheta$ are the time posterior probabilities calculated according to the time interval of the current ray under $M_0$ and $M_1$, respectively, which are also the decision function of γ-ray decision making.

Step 8: Updating of the Time Prior Probability $$\vartheta_{i,0} = p_{i,0}^\vartheta;$$

$$\vartheta_{i,1} = p_{i,1}^\vartheta;$$

Step 9: γ-Ray Decision Making

The decision functions of time and energy in the ROI$_i$ are combined. To sum up, the decision on the existence of γ rays is made, specifically:

$$\begin{cases} \text{Action1:} & \text{if } P_{i,0}^{\pi} < P_{i,low\_th}^{\pi} \text{ \& } P_{i,0}^{\vartheta} < P_{i,low\_th}^{\vartheta}, \\ & \text{the signal is judged as a chacteristic } \gamma\text{-ray signal} \\ \text{Action2:} & \text{if } P_{i,0}^{\pi} > P_{i,up\_th}^{\pi} \text{ \& } P_{i,0}^{\vartheta} > P_{i,up\_th}^{\vartheta}, \\ & \text{the signal is judged is a background signal} \\ \text{Action3:} & \text{if } P_{i,0}^{\pi} < P_{i,low\_th}^{\pi} \text{ \& } P_{i,0}^{\vartheta} > P_{i,up\_th}^{\vartheta}, \\ & \text{the signal is judged as a} \\ & \text{natural background radioactive ray signal} \\ \text{Action4:} & \text{if } P_{i,0}^{\pi} > P_{t,up\_th}^{\pi} \text{ \& } P_{t,0}^{\vartheta} < P_{t,low\_th}^{\vartheta}, \\ & \text{the signal is judged as a Compton signal of other} \\ & \text{high-energy rays in this } ROI_i \text{ interval} \\ \text{Action5:} & \text{in other cases,} \\ & \text{no judgement is made, and continue to detect} \end{cases}$$

where $P_{i,up\_th}^{\pi}$ and $P_{i,low\_th}^{\pi}$ are the upper and lower thresholds of the energy decision function, respectively, $P_{i,up\_th}^{\vartheta}$ and $P_{i,low\_th}^{\vartheta}$ are the upper and lower thresholds of the time decision function, respectively.

$$p_{i,up\_th}^{\pi} = \frac{1-\alpha^{\pi}}{1-\alpha^{\pi}+\beta^{\pi}}$$

$$p_{i,low\_th}^{\pi} = \frac{\alpha^{\pi}}{1-\beta^{\pi}+\alpha^{\pi}}$$

$$p_{i,up\_th}^{\vartheta} = \frac{1-\alpha^{\vartheta}}{1-\alpha^{\vartheta}+\beta^{\vartheta}}$$

$$p_{i,low\_th}^{\vartheta} = \frac{\alpha^{\vartheta}}{1-\beta^{\vartheta}+\alpha^{\vartheta}}$$

where $\alpha^{\pi}$ and $\beta^{\pi}$ are the probabilities of making a first type of mistakes and a second type of mistakes in the energy threshold decision making, respectively, and $\alpha^{\vartheta}$ and $\beta^{\vartheta}$ are the probabilities of making the first type of mistakes and the second type of mistakes in the time threshold decision making, respectively.

Step 10: Calculation of the Joint Decision Function of Radionuclide $I_x$ $$P_X = \sum_m \lambda_m \cdot P_{m,0}^{\pi} \cdot P_{m,0}^{\vartheta}$$

$$\lambda_m = \frac{\eta_m \cdot \kappa_m}{\sum_N \eta_N \cdot \kappa_N}$$

where $P_X$ denotes the decision function of nuclide $I_X$, m denotes the serial number of the characteristic γ-ray of nuclide $I_X$, $\lambda_m$ denotes the weight coefficient of the corresponding γ-ray, $p_{m,0}^{\pi}$ and $p_{m,0}^{\vartheta}$ denote the decision functions of energy and time corresponding to the ray, respectively, $\eta_m$ and $\kappa_m$ denote the branching ratio and the intrinsic detection efficiency of γ-ray, respectively, and N is the total number of γ-rays of radionuclide $I_X$.

Step 11: Radionuclide Decision Making

To sum up, the decision is made as follows:

$$\begin{cases} \text{If, } P_X \leq P_{X,low\_th}, \text{ it is judged that there is nuclide } I_x \\ P_{X,up\_th} > P_X > P_{X,low\_th}, \text{ no judgment is made,} \\ \quad \text{and more information is needed} \\ P_{X,up\_th} \leq P_X, \text{ it is judged that there is no nuclide } I_x \end{cases}$$

where $P_{X,up\_th}$ and $P_{X,low\_th}$ are the upper threshold and the lower threshold, respectively. The lower threshold $P_{X,low\_th}$ is a first predefined value, and the upper threshold $P_{X,up\_th}$ is a second predefined value, where the second predefined value is greater than the first predefined value.

$$P_{X,low\_th} = \frac{\alpha}{1-\beta+a}, P_{X,up\_th} = \frac{1-\alpha}{1-\alpha+\beta},$$

where α and β are the probabilities of making a first type of mistakes and a second type of mistakes in the nuclide joint decision making, respectively. The specific values of α and β need to be determined based on the practical environment, purpose, objectives, and monitoring requirements (confidence level 1–α). Usually, α means "false alarm", and α usually is set as 5%, 10%, etc. For scenarios with high monitoring requirements, α can be set as 1%. β means "missed alarm", which is a more concerned indicator. Generally, β is set as 5%, 10%, etc. For scenarios with high monitoring requirements, β can be set as 1%.

Based on the above description, compared with the prior art, the present disclosure has the following characteristics.

1) The construction of the probability density functions of the null hypothesis and the alternative hypothesis is one of the key points of the present disclosure. In the present disclosure, the hypothesis about whether there are radionuclides is converted into whether there are full energy peaks in the ROI based on the single-energy decomposition theory and a certain transformation.

2) The construction method of the probability density function of energy-related statistics is one of the key points of the present disclosure. The probability density function of the energy in the actual process is actually a linear superposition of Gaussian distribution, uniform distribution and triangular distribution according to their respective counting rate shares and is not limited to Gaussian distribution and uniform distribution in the example of the present disclosure. The specific probability density distribution can be determined according to the actual use scene.

3) The construction of prior probabilities of energy-related statistics and time-related statistics is one of the key points of the present disclosure. In the present disclosure, the prior probability density function can be a non-informative prior probability density function or a conjugate prior probability density function, and is not limited to the noninformative prior probability density function in the present disclosure. At the same time, the initial value of the prior probabilities can be determined according to the actual situation, including but not limited to the parameters (0.5, 0.5) in the example of the present disclosure.

4) The construction of the decision function of energy-related statistics and time-related statistics is one of the key points of the present disclosure. In the present disclosure, the decision function can be constructed using two paths: a) the decision function is obtained according to the prior probability and the sample probability density function; b) in the construction process, the Bayesian factor can first be calculated and obtained according to the sample probability density function, and then the decision function is jointly constructed according to the prior probability and the Bayesian factor. No matter which path it is, the decision function structure constructed according to the above key information is the key point to be protected in the present disclosure. [The Bayesian factor, as an intermediate parameter, may not participate in the construction process in the actual construction process.]
5) The solution of the decision function is one of the key points of the present disclosure, no matter whether it is calculated according to the prior probability and the Bayesian factor or it is directly calculated according to the prior information and the sample information. In the process of calculation based on the prior probability and the Bayesian factor, the Bayesian factor, as an intermediate parameter, may not participate in the calculation process in actual use.
6) The construction method of threshold determination at the end of statistical inference of energy-related statistics and time-related statistics is one of the key points of the present disclosure. In the conventional Bayesian method, the relative size of the posterior probabilities of the null hypothesis and the alternative hypothesis (i.e. the upper and lower thresholds are both 0.5) is generally selected, that is, the probability ratio test (SPRT). When making statistical decisions, in the case of the posterior probabilities of the null hypothesis and the alternative hypothesis are close to each other, a wrong decision may be made with a great probability. In the present disclosure, the upper and lower thresholds are set to different values for the decision functions of the energy and the time interval (for example, the decision thresholds for the ROI are 0.8 and 0.2 in this example, which does not mean that the specific values are the protection points of the present disclosure), thus significantly improving the accuracy of the decision results. At the same time, the introduction of decision thresholds for two types of decisions of the decision function (supporting the null hypothesis and supporting the alternative hypothesis) is the protection point of the present disclosure, and the selection of specific values of the thresholds can be made according to actual use scenes.
7) It is one of the key points of the present disclosure to use the combined discrimination result of energy-related statistics and time-related statistics of the detected γ ray as the discrimination result of this γ ray. In combination with the content in 6), although there are ways that identify nuclides by combining time and energy in the prior art, the probability density function and the decision function used in these ways are different from those used in the present disclosure.
8) It is one of the key points of the present disclosure to construct the decision function of nuclides according to the product of all γ-ray decision functions of radionuclides and the constructed weight coefficient. The same or similar methods are not disclosed in the prior art.
9) In the statistical decision of the decision function, the upper and lower thresholds are set to different values, thereby significantly improving the accuracy of decision results. At the same time, the introduction of decision thresholds for two types of decisions of the decision function (supporting the null hypothesis and supporting the alternative hypothesis) is one of the key points of the present disclosure, and the selection of specific values of the thresholds can be made according to the actual use scenes.
10) In the construction of the weight coefficient of the decision function, the normalized result of the product of the branching ratio of the ray and the intrinsic detection efficiency in the corresponding nuclide is taken as the weight coefficient in the nuclide.

Taking background, $^{241}$Am, $^{137}$Cs as examples, the specific implementation process of the nuclide identification method according to the present disclosure will be described hereinafter. The lanthanum bromide (LaBr$_3$) γ spectrometer is used as an example, and any γ spectrometer can be selected in the actual operation process.

Embodiment 1

In this example, a 1.5-inch LaBr$_3$(Ce) detection system is used, and the energy scale and the half-width scale are:

$$E=0.07525 \cdot ch+0.9285 (R^2=1)$$

$$\text{FWHM}=2.75077+0.56398 \cdot \sqrt{E+1.57004 \cdot E^2}$$

A nuclide library containing 22 nuclides and 46 characteristic gamma rays is constructed. Accordingly, 46 ROIs are delineated in the whole spectrum. The ROI is taken as full width at tenth maximum (FWTM). The coverage factor is k=2.146, the confidence is about 96.8%, and the energy width of the ROI$_i$ is $\Delta E_i=4.296 \cdot \sigma_i$. The background data is acquired, the background counting rate of the whole spectrum of the scale is $\dot{n}_{bkg} \approx 59.1 \, s^{-1}$, and the background counting rate in 46 ROIs is $\dot{n}_{i,bkg}$.

Due to the unbiasedness of the prior probability, the initial value of the prior probability is set to (0.5, 0.5). The lower limit of detection sensitivity of this method in the ROI$_i$ is set as 30%, in which $\tau_{i,min}=50\% \cdot \tau_{i,bkg}$, $\alpha^\pi=\beta^\pi=0.2$ and $\alpha^\vartheta=\beta^\vartheta=0.2$ are set. The upper and lower thresholds of making decisions are $P_{i,up\_th}^\pi=P_{i,up\_th}^\vartheta=0.8$, $P_{i,low\_th}^\pi=P_{i,low\_th}^\vartheta=0.2$, $P_{X,up\_th}=0.64$, and $P_{X,low\_th}=0.04$.

Based on this, the background is identified.

The detector has detected the first ray, and the time and energy information is (0.045657025, 44)/(time/second, energy/channel).

Based on above Step 1 according to the present disclosure, it is concluded that the ray belongs to ROI$_1$ (33, 51) corresponding to the 32 keV ray and ROI$_2$ (38, 58) corresponding to the 35 keV ray.

The energy Bayesian factors of ROI$_1$ and ROI$_2$ are calculated in Step 2, which are: $B_1^\pi(\vartheta_{1,1})=0.6417$ and $B_2^\pi(\vartheta_{2,1})=0.8062$.

The energy decision functions of ROI$_1$ and ROI$_2$ are calculated in Step 3, which are: $p_{1,0}^\pi=0.3909$ and $p_{2,0}^\pi=0.4464$.

The energy prior probabilities of ROI$_1$ and ROI$_2$ are updated in Step 4, which are: $\pi_{1,0}=0.3909$ and $\pi_{2,0}=0.4464$.

The time intervals, the time Bayesian factors and the time decision functions of ROI$_1$ and ROI$_2$ are calculated in Steps 5 to 8, which are:

$$\Delta t_1=0.0457, B_1^\vartheta(\Delta t_1)=0.8858, p_{1,0}^\vartheta=0.4697; \text{ and}$$

$$\Delta t_2=0.0457, B_2^\vartheta(\Delta t_2)=1.0280, P_{2,0}^\vartheta=0.5069$$

A decision is made on the 32 keV characteristic γ ray corresponding to ROI$_1$ and the 35 keV characteristic γ ray corresponding to ROI$_2$ in Step 9.

Because $p_{1,0}^\pi=0.3909$ and $p_{1,0}^\vartheta=0.4697$, ROI$_1$ makes no decision and waits for the next ray. Because $p_{2,0}^\pi=0.4464$ and $p_{2,0}^\vartheta=0.5069$, ROI$_2$ makes no decision and waits for the next ray.

It is assumed that it is determined in Step 9 that there is 32 keV characteristic γ ray corresponding to ROI$_1$ or ROI$_1$ is the background signal. Since the 32 keV ray belongs to radionuclide $^{133}$Ba, it is necessary to investigate whether there is radionuclide $^{133}$Ba at this time.

In Step 10, the time and energy decision functions of $ROI_1$, $ROI_5$, $ROI_{17}$, $ROI_{18}$, $ROI_{22}$ and $ROI_{23}$ corresponding to characteristic γ rays of 32 keV, 81 keV, 276 keV, 302 keV, 356 keV and 383 keV are used to calculate the joint decision function of the radionuclide $^{133}$Ba.

In Step 11, radionuclides are identified according to the joint decision function of $^{133}$Ba.

After the arrival of the next ray, Step 1 to Step 8 are repeated according to the time and energy information of the ray to calculate the time and energy decision functions of the corresponding ROI. Thereafter, Step 9 is repeated to identify the characteristic γ rays. Finally, Step 10 is repeated to identify radionuclides.

In this example, a total of $10^4$ radiation particles are measured and identified, with a total time of 166.25 seconds and a full-spectrum counting rate of 60.15 $s^1$.

In order to explain the process of nuclide identification in detail, take the 3424-th ray detected by the detector as an example (that is, the ray particle when it is determined for the first time that there is no 661 keV characteristic γ ray and the corresponding nuclide $^{137}$Cs), so as to observe the changes of the γ-ray decision function and the nuclide joint decision function before and after this ray.

The detector has detected the 3424-th ray, and the time and energy information is (57.8514355, 881)/(time/second, energy/channel). At this time, the prior probabilities of energy and time are updated to $\pi_{31,0}$=0.999975 and $\vartheta_{31,0}$=0.6936.

According to Step 1, it is concluded that this ray belongs to $ROI_{31}$ (857,900) corresponding to the ray with energy of 661 keV.

The energy Bayesian factor of $ROI_{31}$ is calculated in Step 2, which is $B_{31}^\pi(\vartheta_{31,28})$=0.6251.

The energy decision function of $ROI_{31}$ is calculated in Step 3, which is $p_{31,0}^\pi$=0.999960.

The energy prior probability of $ROI_{31}$ is updated in Step 4, which is $\pi_{31,0}$=0.999960.

The time interval, the time Bayesian factor and the time decision function of $ROI_{31}$ are calculated in Step 5 to Step 8, which are:

$$\Delta t_{31}=0.0042, B_{31}^\vartheta(\Delta t_{31})=1.8946, \text{ and } p_{31,0}^\vartheta=0.8109$$

A decision is made on the 661 keV characteristic γ ray corresponding to $ROI_{31}$ in Step 9. Because $p_{31,0}^\pi$=0.999960>$P_{31,up\_th}^\pi$=0.8 and $p_{31,0}^\vartheta$=0.8109>$P_{31,up\_th}^\vartheta$=0.8, a determination is made that all $ROI_{31}$ signals come from the background. Because the characteristic energy corresponding to $ROI_{31}$ signals is 661 keV, the corresponding characteristic γ ray belongs to nuclide $^{137}$Cs. Thereafter, the joint decision function of nuclide $^{137}$Cs needs to be calculated to judge whether there is nuclide $^{137}$Cs for updating.

The joint decision function of nuclide $^{137}$Cs is calculated in Step 10, which is: $P_{^{137}Cs}$=0.8109.

In Step 11, a decision is made on whether there is nuclide $^{137}$Cs. Because $P_{^{137}Cs}$=0.8109>$P_{^{137}Cs,up\_th}$=0.64, a judgment is made that there is no nuclide $^{137}$Cs. Because the nuclide $^{137}$Cs has only one 661 keV characteristic γ ray, the decision on that there is no nuclide $^{137}$Cs can be made when all the $ROI_{31}$ signals come from the background in Step 8. The joint decision function of the nuclide $^{137}$Cs is calculated here only to explain the detailed process of nuclide identification.

Figure 3:
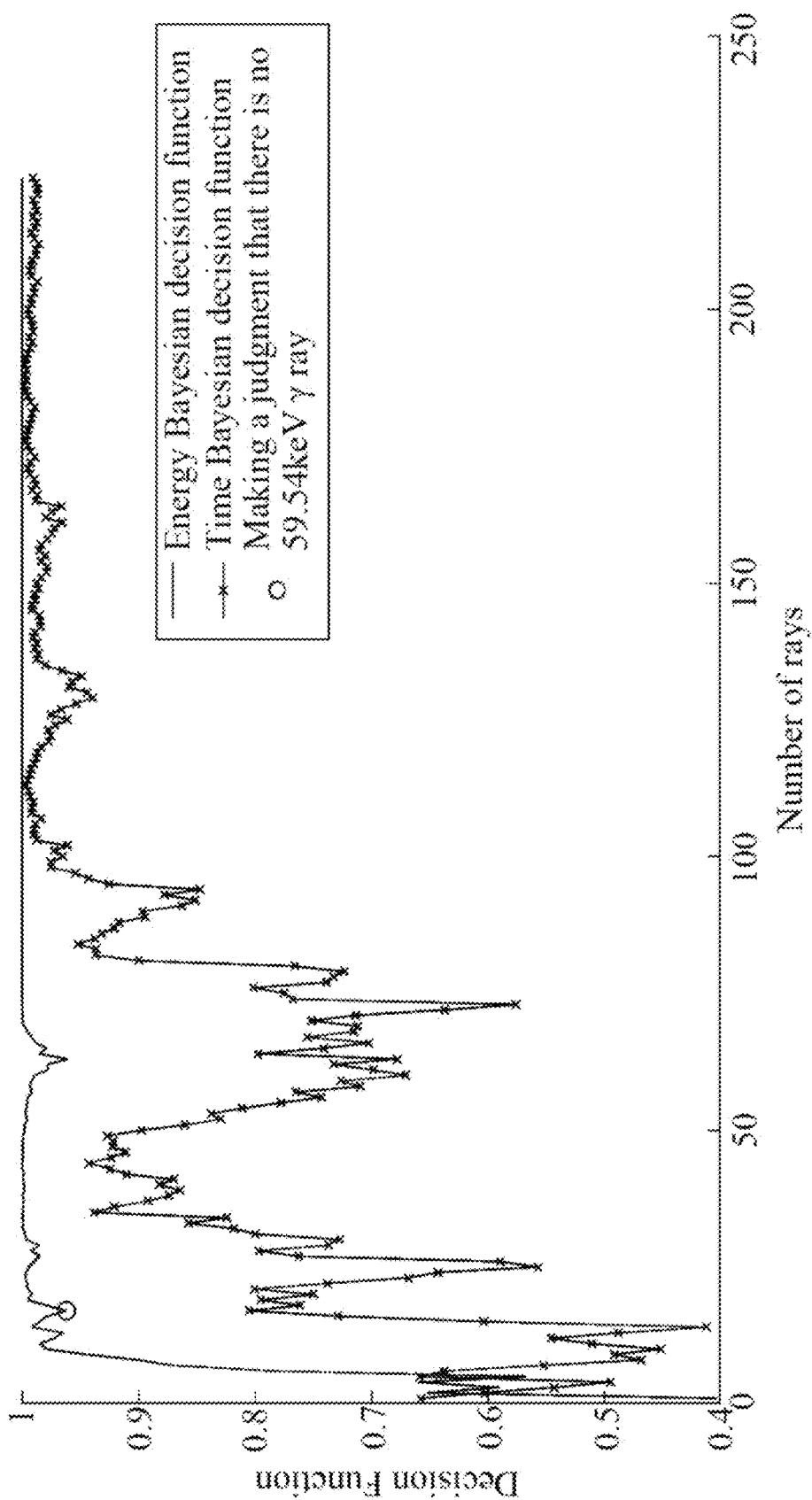
FIG. 3 is a curve diagram illustrating variations of time and energy decision functions of a first 59 keV γ ray according to the present disclosure.
Figure 4:
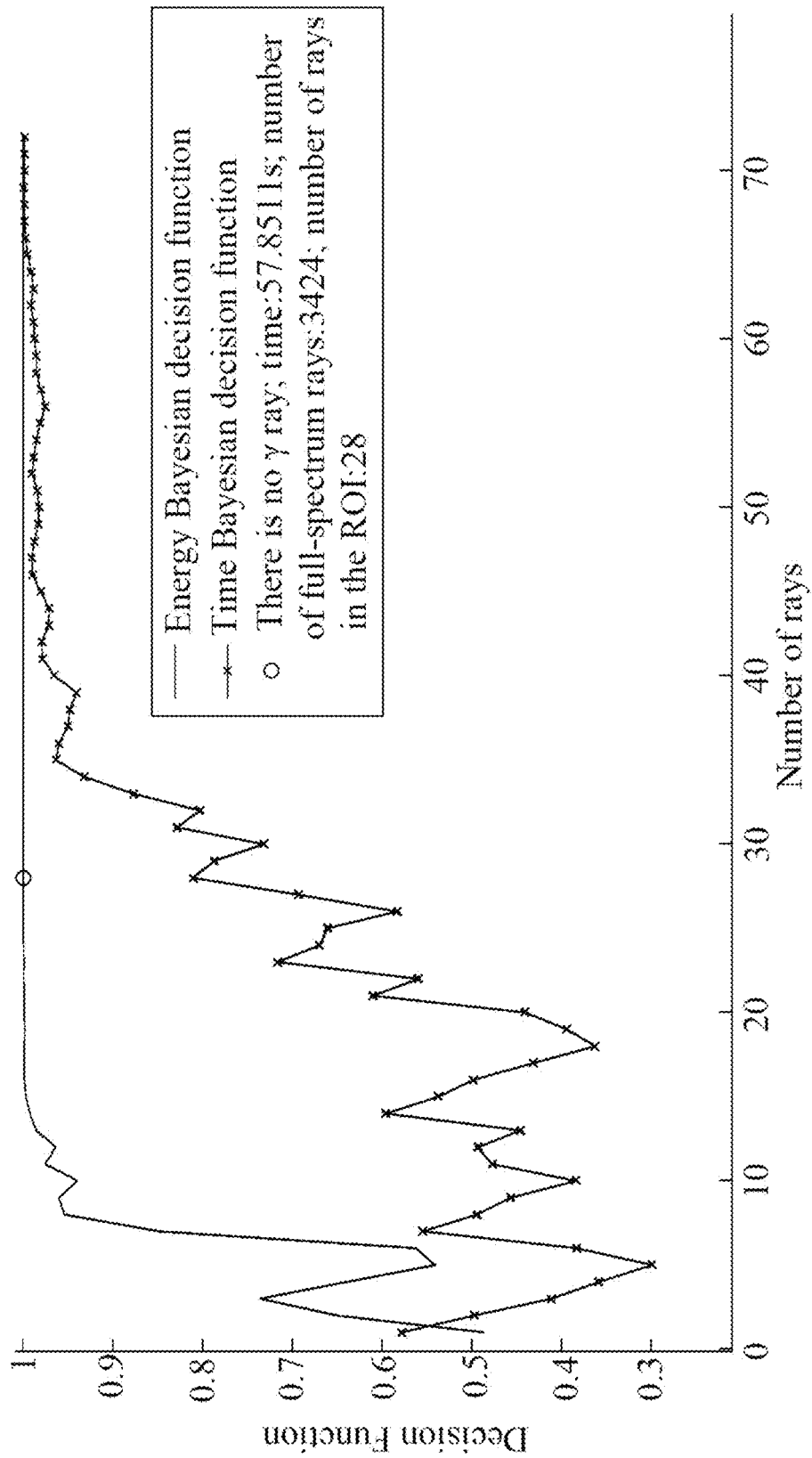
FIG. 4 is a curve diagram illustrating variations of time and energy decision functions of a first 661 keV γ ray according to the present disclosure.
Figure 5:
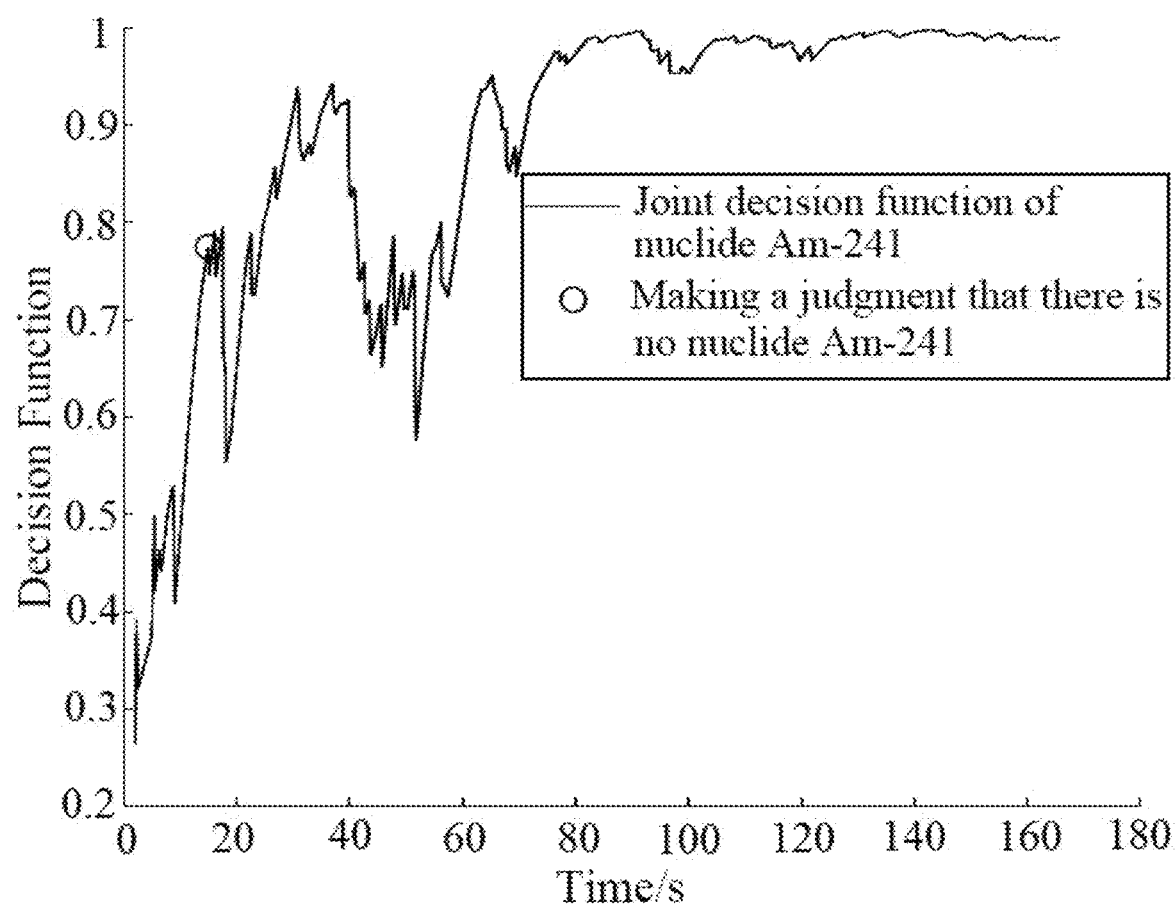
FIG. 5 is a curve diagram illustrating a variation of a first nuclide joint decision function of $^{241}$Am according to the present disclosure.
Figure 6:
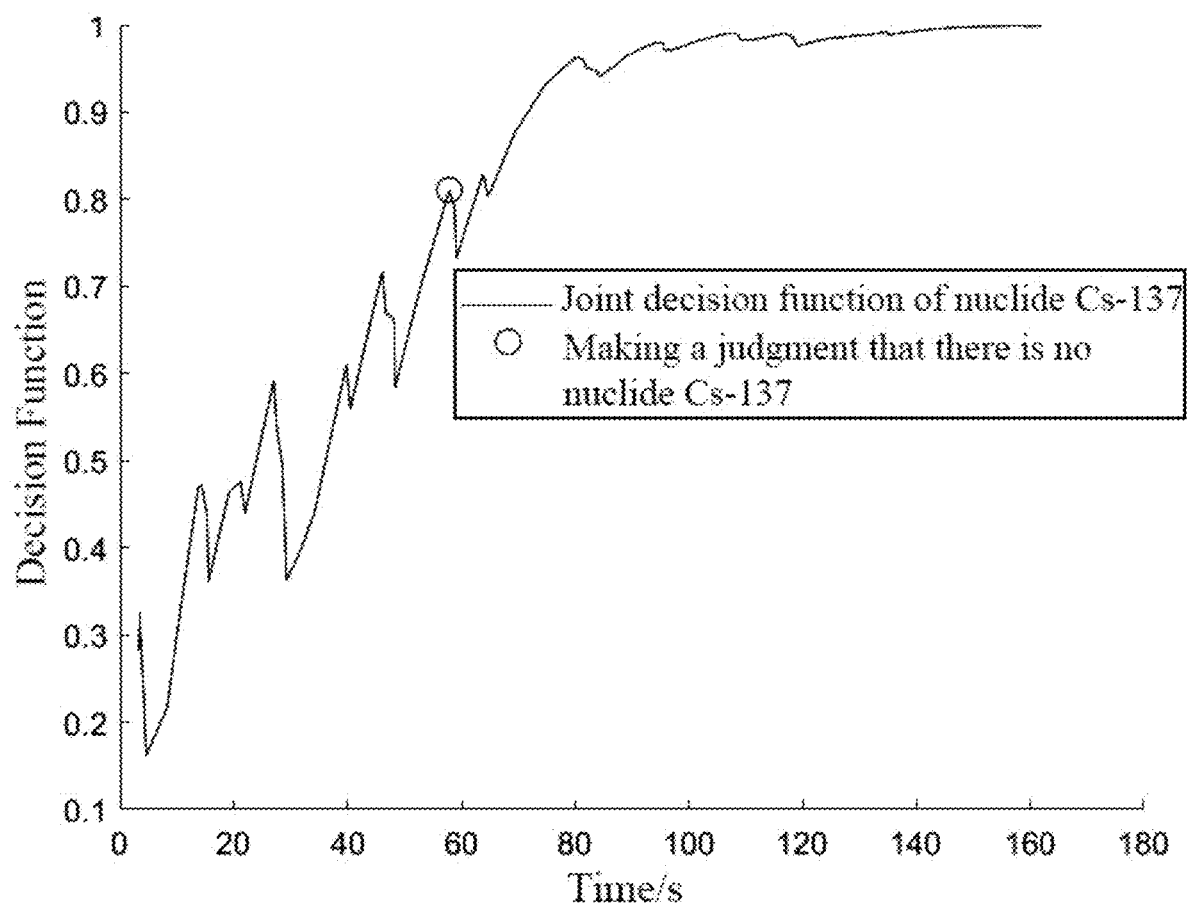
FIG. 6 is a curve diagram illustrating a variation of a first nuclide joint decision function of $^{137}$Cs according to the present disclosure.

It is determined that there are no nuclide $^{241}$Am and its 59 keV characteristic γ ray at the same time in 14.9575 seconds (a total of 881 samples and 17 $ROI_4$ samples). It is determined that there are no nuclide $^{137}$Cs and its 661 keV characteristic γ ray at the same time in 57.8611 seconds (a total of 3424 samples and 28 $ROI_{31}$ samples). The changes of two γ ray decision functions with time are shown in FIGS. 3 and 4. The changes of the nuclide joint decision functions of $^{241}$Am and $^{137}$Cs with time are shown in FIGS. 5 and 6. In FIG. 3, the final identification result shows that: there is no 59.54 keV γ ray, the spent time is 14.9757 s, the number of full-spectrum rays is 881, and the number of rays in ROI is 17. In FIG. 4, the final identification result shows that: there is no 661 keV γ ray, the spent time is 57.8511 s, the number of full-spectrum rays is 3424, and the number of rays in ROI is 28. In FIG. 5, the final identification result shows that there is no nuclide Am-241. In FIG. 6, the final identification result shows that there is no nuclide Cs-137.

In addition, under the background condition, there is no incident of radionuclide false alarm (the false alarm is defined as: there is no radionuclide, but it is judged that there is radionuclide). When it is determined that the above two characteristic γ rays do not exist and all the signals in the corresponding ROI come from the background, the time required is too long because the sample collection rate in the ROI corresponding to the characteristic γ ray under the background condition is too low. When making an effective determination, it can be found by observation of the number of samples collected in the ROI that effective identification can be made if a small number of samples are collected in the ROI.

Embodiment 2

Components and parameters used in this embodiment are the same as those in Embodiment 1 described above. There is the identification result of $^{137}$Cs (9.22*$10^3$Bq) (the distance between the source and the front end of the detector is 35 cm) (the equivalent dose rate is about 5.52 nGy/h).

The detector detects the first ray, and the time and energy information is (0.030928838, 161)/(time/second, energy/channel).

According to Step 1, it is concluded that the ray belongs to $ROI_8$ (150, 171) corresponding to the 122 keV ray.

The energy Bayesian factor of the $ROI_8$ is calculated in Step 2, which is: $B_1^\pi(\varepsilon_{1,1})$=0.6258.

The energy decision function of the $ROI_8$ is calculated in Step 3, which is: $p_{1,0}^\pi$=0.3849.

The energy prior probability of the $ROI_8$ is updated in Step 4, which is: $\pi_{1,0}$=0.3849.

The time interval, the time Bayesian factor and the time decision function of the $ROI_8$ are calculated in Steps 5 to 8, respectively, which are:

$$\Delta t_1=0.0309, B_1^\vartheta(\Delta t_1)=0.7079 \text{ and } p_{1,0}^\vartheta=0.4145$$

In Step 9, a decision is made on the 122 keV ray corresponding to $ROI_8$. Because $p_{1,0}^\pi$=0.3849 and $p_{1,0}^\vartheta$=0.4145, $ROI_8$ makes no decision and waits for the next ray.

If it is determined in Step 8 that there is γ ray, assuming that there is the 122 keV ray corresponding to ROTS, it is necessary to investigate whether there are radionuclides $^{57}$Co and $^{152}$Eu at this time, specifically as follows.

In Step 10, the time and energy decision functions of $ROI_8$ and $ROI_{10}$ corresponding to the 122 keV ray and the 136 keV ray are used to calculate the joint decision function of nuclide $^{57}$Co. The time and energy decision functions of $ROI_8$, $ROI_{16}$, $ROI_{21}$, $ROI_{32}$, $ROI_{36}$, and $ROI_{42}$ corresponding to 122 keV, 244 keV, 344 keV, 779 keV, 964 keV and 1408 keV are used to calculate the joint decision function of nuclide $^{152}$Eu.

In Step 11, according to the joint decision function of $^{57}$Co and $^{152}$Eu, the determination of the hypothesis test of the existence of two radionuclides is made.

After the arrival of the next ray, Step 1 to Step 8 are repeated according to the time and energy information of the ray to calculate the time and energy decision functions of the corresponding ROI. Thereafter, Step 9 is repeated to identify the γ rays. Finally, Step 10 and Step 11 are repeated to identify radionuclides.

In this example, a total of $10^4$ radiation particles are measured and identified, with a total time cost of 153.70 seconds and a full-spectrum counting rate of 64.14 s$^{-1}$.

In order to explain the process of nuclide identification in detail, take the 281st ray detected by the detector as an example (that is, the ray particle when it is determined for the first time that there is 661 keV characteristic γ ray and the nuclide $^{137}$Cs), so as to observe the changes of the γ-ray decision function and the nuclide joint decision function before and after this ray.

The detector has detected the 281st ray, and the time and energy information is (4.260600813, 865)/(time/second, energy/channel). At this time, the prior probabilities of energy and time are updated to $\pi_{31,0}$=0.1818 and $\vartheta_{31,0}$=0.2220.

According to Step 1, it is concluded that this ray belongs to ROI$_{31}$ (857,900) corresponding to 661 keV ray.

The energy Bayesian factor of ROI$_{31}$ is calculated in Step 2, which is: $B_{31}^{\pi}(\varepsilon_{31,28})$=1.3158.

The energy decision function of ROI$_{31}$ is calculated in Step 3, which is $p_{31,0}^{\pi}$=0.1818.

The energy prior probability of ROI$_{31}$ is updated in Step 4, which is $\pi_{31,0}$=0.1818.

The time interval, the time Bayesian factor and the time decision function of ROI$_{31}$ are calculated in Step 5 to Step 8, respectively, which are:

$$\Delta t_{31}=0.0075, B_{31}^{\vartheta}(\Delta t_{31})=0.6932, \text{ and } p_{31,0}^{\vartheta}=0.1698.$$

A decision is made on the 661 keV characteristic γ ray corresponding to ROI$_{31}$ in Step 9. Because $p_{31,0}^{\pi}$=0.1818<$P_{31,low\_th}^{\pi}$=0.2 and $p_{31,0}^{\vartheta}$=0.1698<$P_{31,low\_th}^{\vartheta}$=0.2, a judgment is made that there is the 661 keV characteristic γ ray. Because the 661 keV characteristic γ ray corresponding to ROI$_{31}$ signals belongs to nuclide $^{137}$Cs, thereafter, the joint decision function of nuclide $^{137}$Cs needs to be calculated to judge whether there is nuclide $^{137}$Cs for updating.

The joint decision function of nuclide $^{137}$Cs is calculated in Step 10, which is: $P_{137_{Cs}}$=0.0309.

In Step 11, a decision is made on whether there is nuclide $^{137}$Cs. Because $P_{137_{Cs}}$=0.0309<$P_{137_{Cs,low\_th}}$=0.04, a determination is made that there is nuclide $^{137}$Cs. Because the nuclide $^{137}$Cs has only one 661 keV characteristic γ ray, the decision on that there is no nuclide $^{137}$Cs can be made when all the ROI$_{31}$ signals come from the background in Step 11. The joint decision function of the nuclide $^{137}$Cs is calculated here only to explain the detailed process of nuclide identification.

Figure 7:
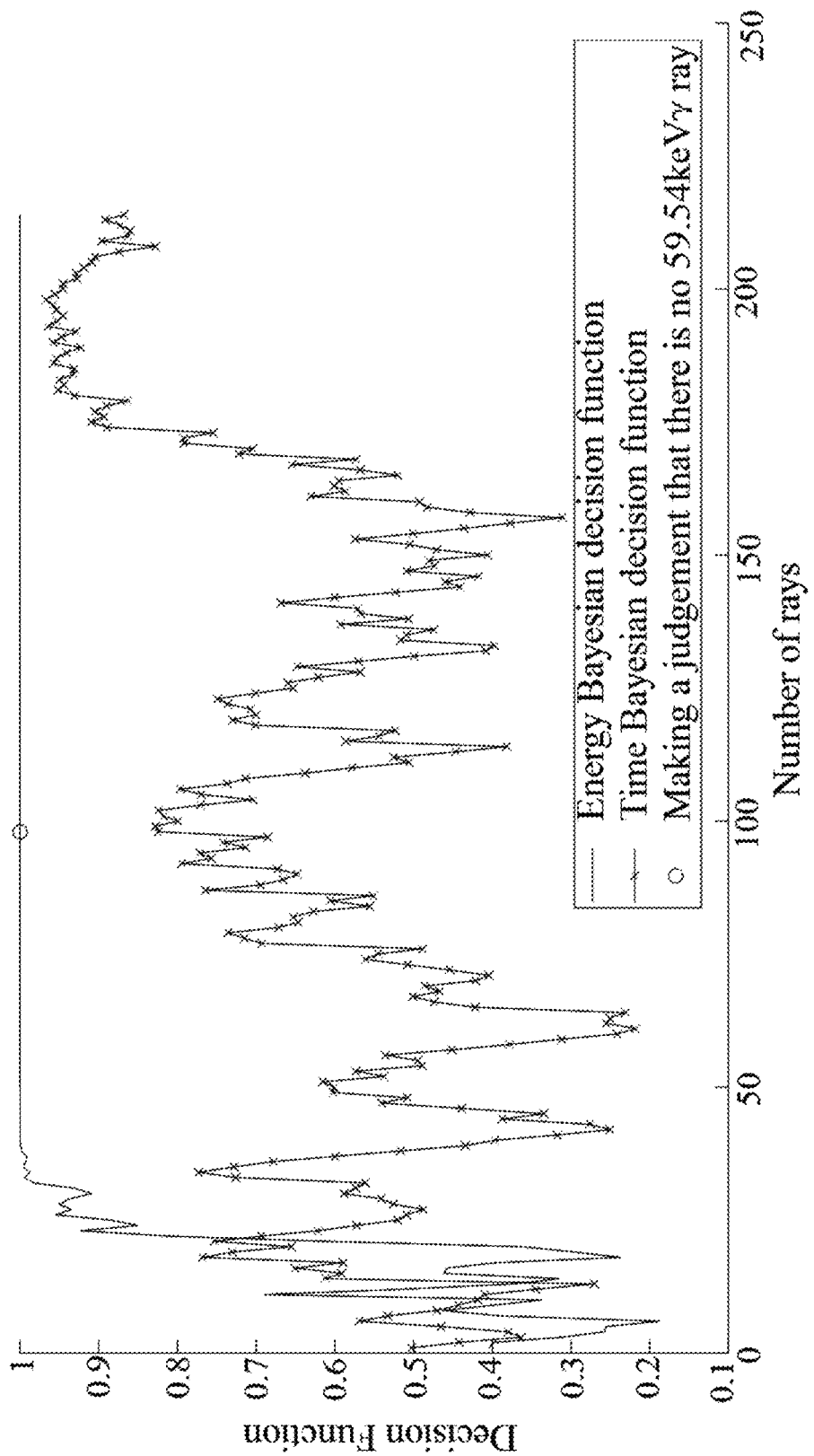
FIG. 7 is a curve diagram illustrating variations of time and energy decision functions of a second 59 keV γ ray according to the present disclosure.
Figure 8:
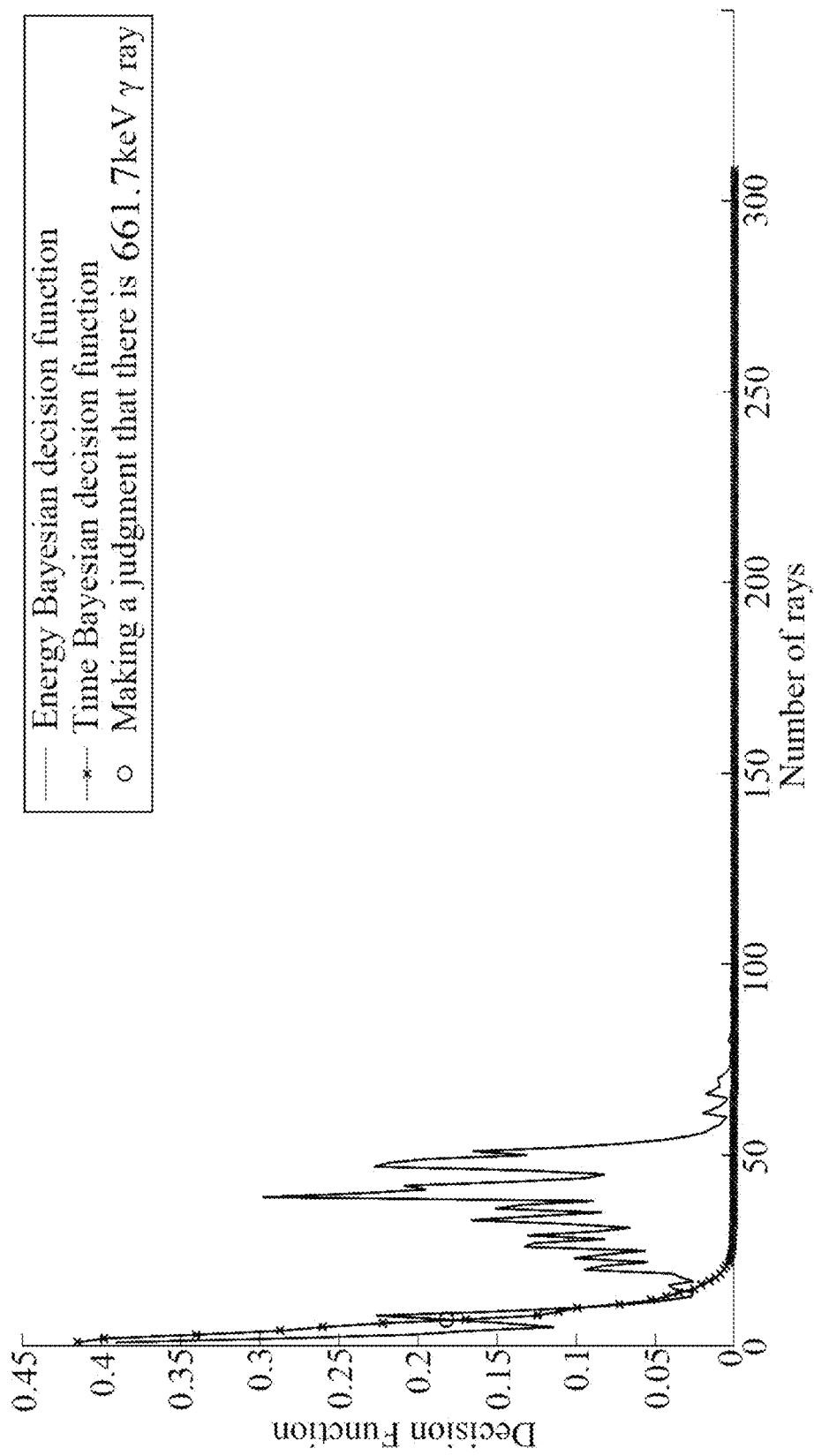
FIG. 8 is a curve diagram illustrating variations of time and energy decision functions of a second 661 keV γ ray according to the present disclosure.
Figure 9:
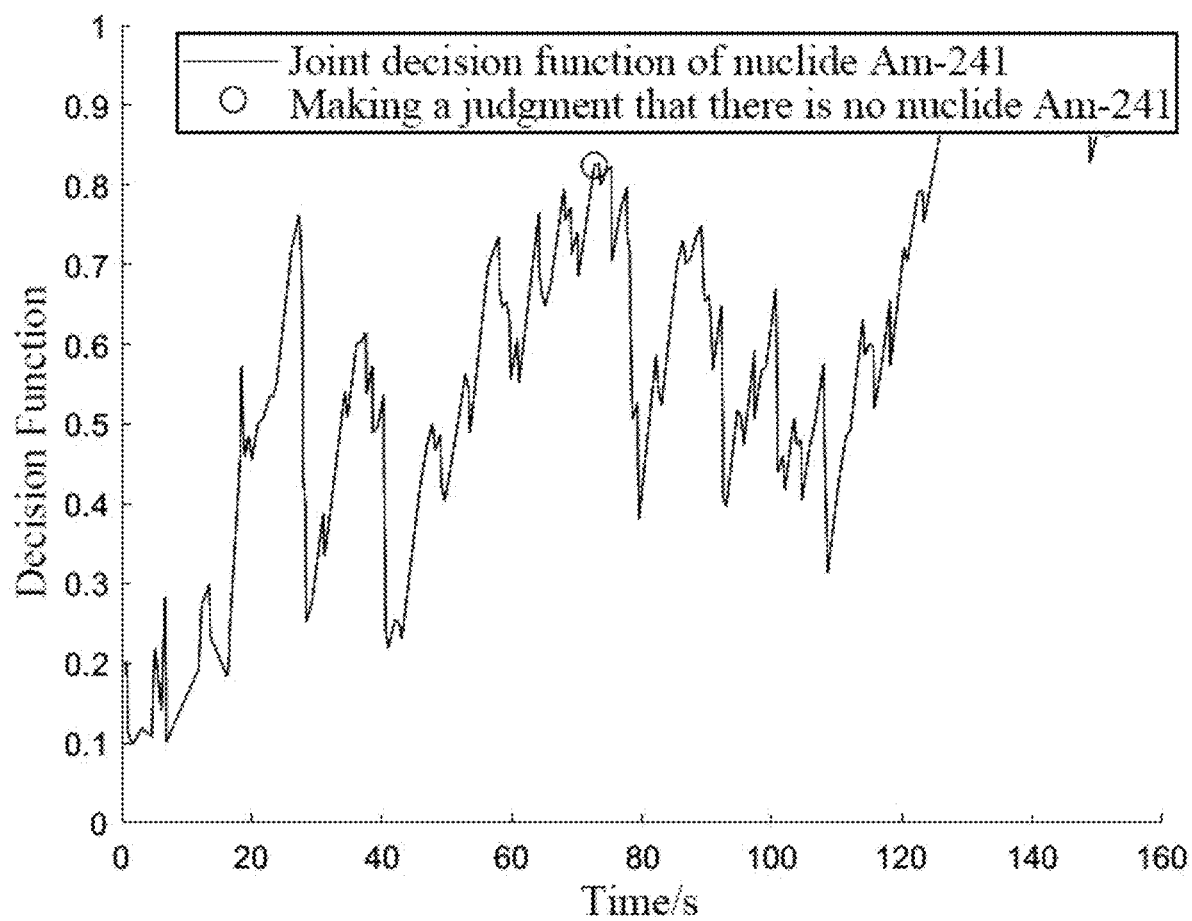
FIG. 9 is a curve diagram illustrating a variation of a second nuclide joint decision function of $^{241}$Am according to the present disclosure.
Figure 10:
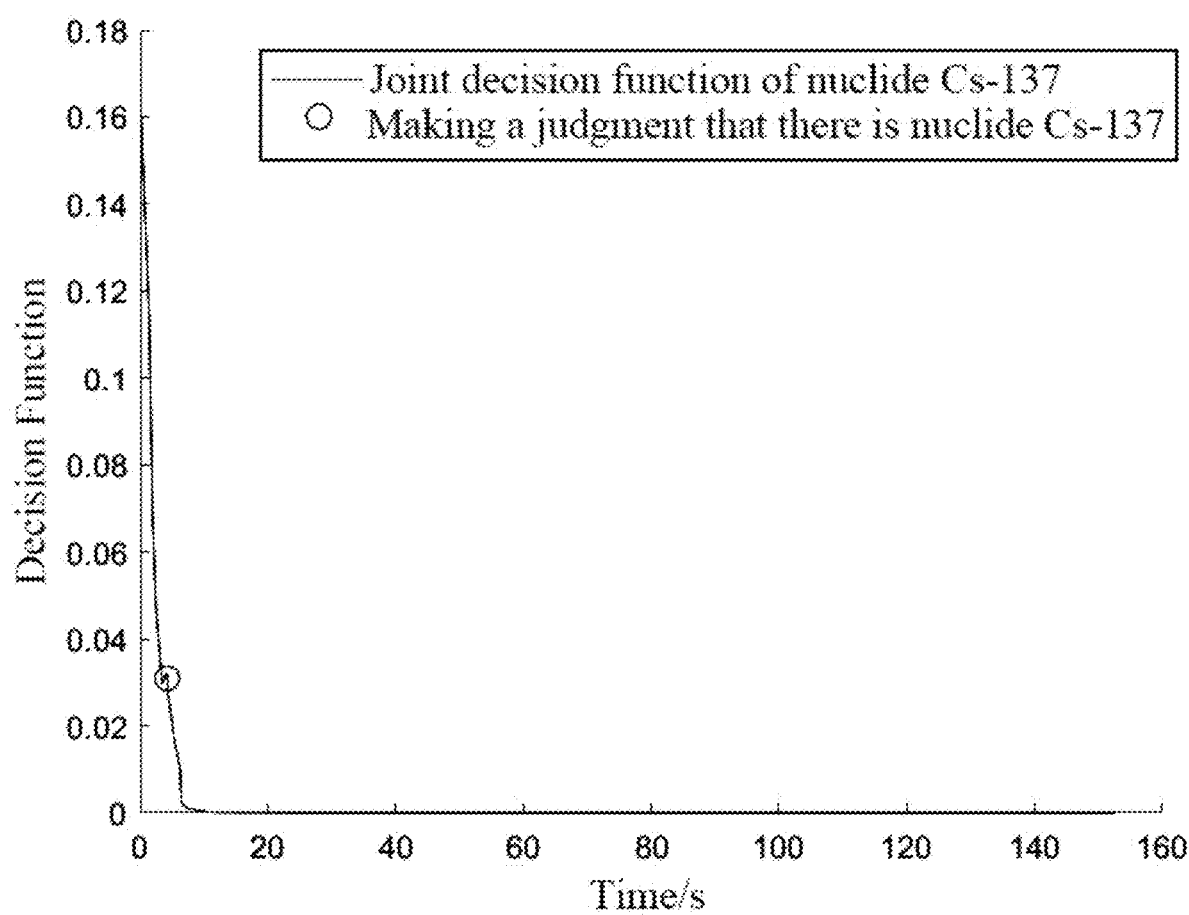
FIG. 10 is a curve diagram illustrating a variation of a second nuclide joint decision function of $^{137}$Cs according to the present disclosure.

It is determined that there are no nuclide $^{241}$Am and its 59 keV characteristic γ ray at the same time in 72.6919 seconds (a total of 4613 samples and 98 ROI$_4$ samples). It is determined that there are nuclide $^{137}$Cs and its 661 keV characteristic γ ray at the same time in 4.2606 seconds (a total of 281 samples and 7 ROI$_{31}$ samples). The changes of two γ ray decision functions with time are shown in FIGS. 7 and 8. The changes of the nuclide joint decision functions of $^{241}$Am and $^{137}$Cs with time are shown in FIGS. 9 and 10. In FIG. 7, the final identification result shows that there is no 59.54 keV γ ray, the spent time is 72.6919 s, the number of full-spectrum rays is 4613, and the number of rays in ROI is 98. In FIG. 8, the final identification result shows that there is 661.7 keV γ ray, the spent time is 4.2606 s, the number of full-spectrum rays is 281, and the number of rays in ROI is 7. In FIG. 9, the final identification result shows that there is no nuclide $^{241}$Am. In FIG. 10, the final identification result shows that there is $^{137}$Cs.

Compared with the nuclide identification process under the above background conditions (namely Embodiment 1 and Embodiment 2), the following content can be found.

Under the conditions of background and $^{137}$Cs radioactive source, the characteristic γ-ray decision function and the nuclide joint decision function of $^{241}$Am are both close to 1, and the determination that there is no characteristic γ-ray and $^{241}$Am nuclide is made. At the same time, under the conditions of background and $^{137}$Cs radioactive source, there is no false alarm event. The Compton count of ROI$_4$ corresponds to 661 keV ray of $^{137}$Cs at 59 keV of $^{241}$Am only influences the speed of its convergence to 1, without influencing its precision (the results of other characteristic gamma rays and corresponding nuclides not corresponding to 661 keV are the same as the determination and identification result of $^{241}$Am).

Under the background condition, the characteristic gamma-ray decision function of $^{137}$Cs quickly approaches to 1, making a determination that there is no characteristic γ ray and making a determination that there is no $^{137}$Cs nuclide. Under the condition that there is $^{137}$Cs nuclide, both the characteristic γ ray decision function and the nuclide joint decision function quickly approach to zero, a determination that there is characteristic γ ray is made and a determination that there is $^{137}$Cs nuclide is made. It can be seen that this example has realized the rapid identification of $^{137}$Cs nuclides (the identification time is 4.2606 seconds, there is a total of 281 samples, and the equivalent dose rate is about 5.52 nGy/h).

The nuclide identification method of the present disclosure significantly is improved in items of the universality, based on a Bayesian principle and a sequential posterior probability, through changing the test model of the nuclide identification method and setting a value range of a time interval on the prior probability, instead of directly assigning a predefined fixed value to the time interval parameter. According to statistical characteristics, a background probability density function and a Compton probability density function in an ROI are determined. An energy Bayesian factor and a time Bayesian factor are determined based on energy and time interval information in a sequence of the nuclear detection events obtained by measurement. By combining the two factors, Compton plateau can be effectively identified and distinguished. Under the same identification conditions and the same confidence level, the method in this disclosure can effectively identify the existence and types of radionuclides faster than an energy spectrum decomposition analysis-characteristic peak matching method. Compared with the fuzzy mathematics and neural network nuclide identification methods, the method in this disclosure is more universal.

In addition, compared with the sequential nuclide identification method based on the Bayesian theory and the sequential probability ratio test published in previous research, aiming at the problem that Compton plateau cannot be distinguished and the universality is poor in previous research, for the sequential Bayesian nuclide identification method based on the Bayesian method and the sequential posterior probability according to the present disclosure, it can be found, according to the above examples, that the false alarm rate and the missed alarm rate are very low, and it shows that the method can effectively identify Compton particles from high-energy rays appearing in the low-energy ROI.

Further, the present disclosure provides a nuclide identification system, which is used to implement the nuclide identification method described above. The system includes: a ray belonging region determining module, a nuclear detection event sequence description module, an energy Bayesian factor determining module, an energy decision function determining module, an ROI time interval determining module, a time Bayesian factor determining module, a time decision function determining module, a decision function combining module, a nuclide joint decision function determining module, and a nuclide identification module. The above modules are modules implemented on computer.

The ray belonging region determining module is configured to acquire time-energy information of a ray, and determine whether the ray belongs to one of ROIs based on energy information in time-energy information of the ray.

The nuclear detection event sequence description module is configured to, when the ray belongs to the one of ROIs, describe a sequence of all the nuclear detection events in the ROI.

The energy Bayesian factor determining module is configured to determine an energy Bayesian factor based on the energy information in the described sequence of all the nuclear detection events.

The energy decision function determining module is configured to determine an energy decision function based on the energy Bayesian factor.

The ROI time interval determining module is configured to determine a time interval in the ROI based on the time information in the described sequence of all the nuclear detection events.

The time Bayesian factor determining module is configured to determine a time Bayesian factor based on the time interval.

The time decision function determining module is configured to determine a time decision function based on the time Bayesian factor.

The decision function combining module is configured to combine the energy decision function and the time decision function to obtain a joint decision function of the ROI.

The nuclide joint decision function determining module is configured to, based on a characteristic γ ray corresponding to the ROI, retrieve a potential nuclide corresponding to the ROI, and combine the joint decision functions of respective ROIs corresponding to the retrieved nuclide to obtain a nuclide joint decision function.

The nuclide identification module is configured to determine and identify the retrieved nuclide based on the nuclide joint decision function.

Still further, the present disclosure further provides an electronic device, which includes a memory and a processor.

A computer program is stored in the memory.

The processor is connected with the memory, and is configured to call and execute the computer program to implement the nuclide identification method described above.

The computer program in the above-mentioned memory can be stored in a computer-readable storage medium when it is implemented in the form of software functional units and sold or used as an independent product. Based on this understanding, according to the present disclosure, the essence of the technical solution or the part that contributes to the prior art or the part of the technical solution can be embodied in the form of a software product, which is stored in a storage medium and includes several instructions to make a computer device (which can be a personal computer, a server or a network device, etc.) execute all or part of the steps of the method described in various embodiments of the present disclosure. The aforementioned storage media include: a USB flash disk, a mobile hard disk, a read-only memory, a random access memory, a magnetic disk or an optical disk and other media that can store program codes.

Further, based on the above description, (1) the nuclide identification method according to the present disclosure can be used in cooperation with various types of detectors, including but not limited to scintillator detectors, semiconductor detectors and other detectors with energy resolution. (2) Parameters such as the number and types of nuclides in the nuclide standard library, the number and importance of γ rays selected by each nuclide are not limited to the form in the example of the present disclosure. (3) The probability density of the energy and the time interval in the process of nuclide identification is not limited to Gaussian distribution and uniform distribution in the example of the present disclosure, and the specific probability density distribution can be determined according to the actual use scene. (4) The initial values of the prior probabilities of the null hypothesis and the alternative hypothesis in the process of nuclide identification can be determined according to the actual situation, including but not limited to the parameters (0.5, 0.5) in the example of the present disclosure. (5) The prior probability density function can be a non-informative prior probability density function or a conjugate prior probability density function, and is not limited to the non-informative prior probability density function in the example of the present disclosure. (6) The selection of the time interval value range in the prior probability is related to background conditions and detector types, including but not limited to the parameters in the example of the present disclosure. (7) In the process of nuclide identification, the upper and lower thresholds are related to the false alarm rate and the missed alarm rate, and their settings can be set according to the actual use scenes and requirements, including but not limited to the parameters in the example of the present disclosure. (8) For the division of the ROI of the full energy peak region, the size of the k value can be set according to the specific situation, including but not limited to the parameters in the example of the present disclosure. (9) The decision function in the present disclosure is solved according to the prior probability and the Bayesian factor, and the Bayesian factor, as an intermediate parameter, may not participate in the calculation process in the actual use calculation process.

Various embodiments of the present disclosure are described in a progressive way, and each embodiment focuses on the description that is different from the other embodiments, and the same and similar parts between various embodiments can be referred to with each other. Since the system disclosed in the embodiment corresponds to the method disclosed in the embodiment, the system is described simply. Refer to the description of the method for the relevant points.

In the present disclosure, specific examples are applied to illustrate the principles and implementations of the present disclosure, and the explanations of the above embodiments are only used to help understand the method and core ideas of the present disclosure. At the same time, according to the idea of the present disclosure, there will be some changes in the specific implementations and application scope for those skilled in the art. To sum up, the contents of the specification should not be construed as limiting the present disclosure.

What is claimed is:

1. A nuclide identification method, comprising:
receiving, at a computer, the time-energy information of a ray from a detector, and performing following steps:
determining whether the ray belongs to one of Region of Interests (ROIs) based on energy information in the time-energy information of the ray;
describing a sequence of all nuclear detection events in the ROI when the ray belongs to the one of the ROIs;
determining an energy Bayesian factor based on energy information in the described sequence of all the nuclear detection events;
determining an energy decision function based on the energy Bayesian factor;
determining a time interval in the ROI based on time information in the described sequence of all the nuclear detection events;
determining a time Bayesian factor based on the time interval;
determining a time decision function based on the time Bayesian factor;
combining the energy decision function and the time decision function to obtain a joint decision function of the ROI;
retrieving a potential nuclide corresponding to the ROI based on a characteristic γ ray corresponding to the ROT, and combining joint decision functions of respective ROIs corresponding to the retrieved nuclide to obtain a nuclide joint decision function;
determining whether the retrieved nuclide exists based on the nuclide joint decision function; and
outputting a result that the retrieved nuclide exists in respond to a determination that a value of the nuclide joint decision function is less than or equal to a first predefined value; or a result that the retrieved nuclide does not exist in respond to a determination that the value of the nuclide joint decision function is greater than or equal to a second predefined value, wherein the second predefined value is greater than the first predefined value; or a result of failure in respond to a determination that the value of the nuclide joint decision function is greater than the first predefined value and less than the second predefined value.

2. The nuclide identification method according to claim 1, wherein the energy Bayesian factor is:

$$B_i^\pi(\varepsilon_{i,j}) = \frac{f_{i,0}(\varepsilon_{i,j}|\sigma_{i,0}^2)}{\int g_{i,1}(\sigma_{i,1}^2) f_{i,1}(\varepsilon_{i,j}|\sigma_{i,1}^2) d(\sigma_{i,1}^2)};$$

wherein $B_i^\pi(\varepsilon_{i,j})$ is a j-th energy Bayesian factor of an i-th ROI, $\varepsilon_{i,j}$ is energy information of a current ray, $f_{i,0}(\varepsilon_{i,j}|\pi_{i,0}^2)$ is an energy probability density function under an energy null hypothesis $H_0$, $f_{i,1}(\varepsilon_{i,j}|\pi_{i,1}^2)$ is an energy probability density function under an energy alternative hypothesis $H_1$, $\sigma_{i,0}^2$ is a standard variance of energy under the energy null hypothesis $H_0$, $\sigma_{i,1}^2$ is a standard variance of the energy under the energy alternative hypothesis $H_1$, and $g_{i,1}(\sigma_{i,1}^2)$ is a probability density function of $\sigma_{i,1}^2$ under the energy alternative hypothesis $H_1$.

3. The nuclide identification method according to claim 1, wherein the energy decision function of the ROI is:

$$p_{i,0}^\pi = \left[1 + \frac{1-\pi_{i,0}}{\pi_{i,0}} \frac{1}{B_i^\pi(\varepsilon_{i,j})}\right]^{-1};$$

$$p_{i,1}^\pi = 1 - p_{i,0}^\pi$$

wherein $p_{i,0}^\pi$ is an energy posterior probability of an i-th ROI under an energy null hypothesis $H_0$, $p_{i,1}^\pi$ is an energy posterior probability of the i-th ROI under an energy alternative hypothesis $H_1$, $\pi_{i,0}$ is an energy prior probability of the i-th ROI under the energy null hypothesis $H_0$, $B_i^\pi(\varepsilon_{i,j})$ is a j-th energy Bayesian factor of the i-th ROI, and $\varepsilon_{i,j}$ is energy information of a current ray.

4. The nuclide identification method according to claim 3, wherein after the determining an energy decision function based on the energy Bayesian factor, the method further comprises:
updating the energy prior probability using the energy decision function.

5. The nuclide identification method according to claim 1, wherein the time Bayesian factor is:

$$B_i^\vartheta(\Delta t_{i,j}) = \frac{g_{i,0}(\Delta t_{i,j}|\tau_{i,0})}{\int h_{i,1}(\tau_{i,1}) \cdot g_{i,1}(\Delta t_{i,j}|\tau_{i,1}) d\tau_{i,1}};$$

wherein $B_{\Delta t}^\vartheta(\Delta t_{i,j})$ is the time Bayesian factor, $g_{i,0}(\Delta t_{i,j}|\tau_{i,0})$ is a time interval probability density function under a time null hypothesis $M_0$, $g_{i,1}(\Delta t_{i,j}|\tau_{i,1})$ is a time interval probability density function under a time alternative hypothesis $M_1$, $\tau_{i,0}$ is a mathematic expectation of a time interval under the time null hypothesis $M_0$, $\tau_{i,1}$ is a mathematic expectation of the time interval under the time alternative hypothesis $M_1$, $h_{i,1}(\tau_{i,1})$ is a probability density function under the time alternative hypothesis $M_1$, and $\Delta t_{i,j}$ is the time interval.

6. The nuclide identification method according to claim 1, wherein the time decision function is:

$$p_{i,0}^\vartheta = \left[1 + \frac{1-\vartheta_{i,0}}{\vartheta_{i,0}} \frac{1}{B_i^\vartheta(\Delta t_{i,j})}\right]^{-1};$$

$$p_{i,1}^\vartheta = 1 - p_{i,0}^\vartheta;$$

wherein $p_{i,0}^\vartheta$ is a time posterior probability of an i-th ROI under a time null hypothesis $M_0$, $p_{i,1}^\vartheta$ is a time posterior probability of the i-th ROI under a time alternative hypothesis $M_1$, $\vartheta_{i,0}$ is a time prior probability of the i-th ROI under the time null hypothesis $M_0$, and $\Delta t_{i,j}$ is the time interval.

7. The nuclide identification method according to claim 6, wherein after the determining a time decision function based on the time Bayesian factor, the method further comprises:
updating the time prior probability based on the time decision function.

8. The nuclide identification method according to claim 1, wherein prior to the combining the energy decision function and the time decision function to obtain a joint decision function of the ROI, the method further comprises:
based on a relationship between a calculation result of the energy decision function and upper and lower thresholds of the energy decision function and a relationship between a calculation result of the time decision func-

21 tion and upper and lower thresholds of the time decision function, obtaining a ray signal identification result in the ROI.

9. A nuclide identification system, which is used to implement the nuclide identification method according to claim 1, comprises:
  a ray belonging region determining module, configured to receive time-energy information of a ray from the detector, and determine whether the ray belongs to one of Region of Interests (ROIs) based on energy information in the time-energy information of the ray;
  a nuclear detection event sequence description module, configured to describe a sequence of all nuclear detection events in the ROI when the ray belongs to the one of the ROIs;
  an energy Bayesian factor determining module, configured to determine an energy Bayesian factor based on energy information in the described sequence of all the nuclear detection events;
  an energy decision function determining module, configured to determine an energy decision function based on the energy Bayesian factor;
  an ROI time interval determining module, configured to determine a time interval in the ROI based on time information in the described sequence of all the nuclear detection events;
  a time Bayesian factor determining module, configured to determine a time Bayesian factor based on the time interval;
  a time decision function determining module, configured to determine a time decision function based on the time Bayesian factor;
  a decision function combining module, configured to combine the energy decision function and the time decision function to obtain a joint decision function of the ROI;
  a nuclide joint decision function determining module, configured to retrieve a potential nuclide corresponding to the ROI based on a characteristic γ ray corresponding to the ROI, and combine joint decision functions of respective ROIs corresponding to the retrieved nuclide to obtain a nuclide joint decision function;
  a nuclide identification module, configured to determine whether the retrieved nuclide exists based on the nuclide joint decision function; and
  an outputting module, configured to output a result that the retrieved nuclide exists in respond to a determination that a value of the nuclide joint decision function is less than or equal to a first predefined value; or a result that the retrieved nuclide does not exist in respond to a determination that the value of the nuclide joint decision function is greater than or equal to a second predefined value, wherein the second predefined value is greater than the first predefined value; or a result of failure in respond to a determination that the value of the nuclide joint decision function is greater than the first predefined value and less than the second predefined value.

10. The nuclide identification system according to claim 9, wherein the energy Bayesian factor is:

$$B_i^\pi(\varepsilon_{i,j}) = \frac{f_{i,0}(\varepsilon_{i,j}|\sigma_{i,0}^2)}{\int g_{i,1}(\sigma_{i,1}^2) f_{i,1}(\varepsilon_{i,j}|\sigma_{i,1}^2) d(\sigma_{i,1}^2)};$$

22 wherein $B_i^\pi(\varepsilon_{i,j})$ is a j-th energy Bayesian factor of an i-th ROI, $\varepsilon_{i,j}$ is energy information of a current ray, $f_{i,0}(\varepsilon_{i,j}|\sigma_{i,0}^2)$ is an energy probability density function under an energy null hypothesis $H_0$, $f_{i,1}(\varepsilon_{i,j}|\sigma_{i,1}^2)$ is an energy probability density function under an energy alternative hypothesis $H_1$, $\sigma_{i,0}^2$ is a standard variance of energy under the energy null hypothesis $H_0$, $\sigma_{i,1}^2$ is a standard variance of the energy under the energy alternative hypothesis $H_1$, and $g_{i,1}(\sigma_{i,1}^2)$ is a probability density function of $\sigma_{i,1}^2$ under the energy alternative hypothesis $H_1$.

11. The nuclide identification system according to claim 9, wherein the energy decision function of the ROI is:

$$p_{i,0}^\pi = \left[1 + \frac{1-\pi_{i,0}}{\pi_{i,0}} \frac{1}{B_i^\pi(\varepsilon_{i,j})}\right]^{-1};$$
$$p_{i,1}^\pi = 1 - p_{i,0}^\pi$$

wherein $p_{i,0}^\pi$ is an energy posterior probability of an i-th ROI under an energy null hypothesis $H_0$, $p_{i,1}^\pi$ is an energy posterior probability of the i-th ROI under an energy alternative hypothesis $H_1$, $\pi_{i,0}$ is an energy prior probability of the i-th ROI under the energy null hypothesis $H_0$, $B_i^\pi(\varepsilon_{i,j})$ is a j-th energy Bayesian factor of the i-th ROI, and $\varepsilon_{i,j}$ is energy information of a current ray.

12. The nuclide identification system according to claim 11, wherein after the determining an energy decision function based on the energy Bayesian factor, the method further comprises:
  updating the energy prior probability using the energy decision function.

13. The nuclide identification system according to claim 9, wherein the time Bayesian factor is:

$$B_i^\vartheta(\Delta t_{i,j}) = \frac{g_{i,0}(\Delta t_{i,j}|\tau_{i,0})}{\int h_{i,1}(\tau_{i,1}) \cdot g_{i,1}(\Delta t_{i,j}|\tau_{i,1}) d\tau_{i,1}};$$

wherein $B_{\Delta t}^\vartheta(\Delta t_{i,j})$ is the time Bayesian factor, $g_{i,0}(\Delta t_{i,j}|\tau_{i,0})$ is a time interval probability density function under a time null hypothesis $M_0$, $g_{i,1}(\Delta t_{i,j}|\tau_{i,1})$ is a time interval probability density function under a time alternative hypothesis $M_1$, $\tau_{i,0}$ is a mathematic expectation of a time interval under the time null hypothesis $M_0$, $\tau_{i,1}$ is a mathematic expectation of the time interval under the time alternative hypothesis $M_1$, $h_{i,1}(\tau_{i,1})$ is a probability density function under the time alternative hypothesis $M_1$, and $\Delta t_{i,j}$ is the time interval.

14. The nuclide identification system according to claim 9, wherein the time decision function is:

$$p_{i,0}^\vartheta = \left[1 + \frac{1-\vartheta_{i,0}}{\vartheta_{i,0}} \frac{1}{B_i^\vartheta(\Delta t_{i,j})}\right]^{-1};$$
$$p_{i,1}^\vartheta = 1 - p_{i,0}^\vartheta;$$

wherein $p_{i,0}^\vartheta$ is a time posterior probability of an i-th ROI under a time null hypothesis $M_0$, $p_{i,1}^\vartheta$ is a time posterior probability of the i-th ROI under a time alternative hypothesis $M_1$, $\vartheta_{i,0}$ is a time prior probability of the i-th ROI under the time null hypothesis $M_0$, and $\Delta t_{i,j}$ is the time interval.

15. The nuclide identification system according to claim 14, wherein after the determining a time decision function based on the time Bayesian factor, the method further comprises:
updating the time prior probability based on the time decision function.

16. The nuclide identification system according to claim 9, wherein prior to the combining the energy decision function and the time decision function to obtain a joint decision function of the ROI, the method further comprises:
based on a relationship between a calculation result of the energy decision function and upper and lower thresholds of the energy decision function and a relationship between a calculation result of the time decision function and upper and lower thresholds of the time decision function, obtaining a ray signal identification result in the ROI.

17. An electronic device, comprising:
a memory in which a computer program is stored; and
a processor, which is connected with the memory, and is configured to call and execute the computer program to implement the nuclide identification method according to claim 1.

18. The electronic device according to claim 17, wherein the energy Bayesian factor is:

$$B_i^\pi(\varepsilon_{i,j}) = \frac{f_{i,0}(\varepsilon_{i,j}|\sigma_{i,0}^2)}{\int g_{i,1}(\sigma_{i,1}^2) f_{i,1}(\varepsilon_{i,j}|\sigma_{i,1}^2) d(\sigma_{i,1}^2)};$$

wherein $B_i^\pi(\varepsilon_{i,j})$ is a j-th energy Bayesian factor of an i-th ROI, $\varepsilon_{i,j}$ is energy information of a current ray, $f_{i,0}(\varepsilon_{i,j}|\sigma_{i,0}^2)$ is an energy probability density function under an energy null hypothesis $H_0$, $f_{i,1}(\varepsilon_{i,j}|\sigma_{i,1}^2)$ is an energy probability density function under an energy alternative hypothesis $H_1$, $\sigma_{i,0}^2$ is a standard variance of energy under the energy null hypothesis $H_0$, $\sigma_{i,1}^2$ is a standard variance of the energy under the energy alternative hypothesis $H_1$, and $g_{i,1}(\sigma_{i,1}^2)$ is a probability density function of $\sigma_{i,1}^2$ under the energy alternative hypothesis $H_1$.

19. The electronic device according to claim 17, wherein the energy decision function of the ROI is:

$$p_{i,0}^\pi = \left[1 + \frac{1-\pi_{i,0}}{\pi_{i,0}} \frac{1}{B_i^\pi(\varepsilon_{i,j})}\right]^{-1};$$

$$p_{i,1}^\pi = 1 - p_{i,0}^\pi$$

wherein $p_{i,0}^\pi$ is an energy posterior probability of an i-th ROI under an energy null hypothesis $H_0$, $p_{i,1}^\pi$ is an energy posterior probability of the i-th ROI under an energy alternative hypothesis $H_1$, $\pi_{i,0}$ is an energy prior probability of the i-th ROI under the energy null hypothesis $H_0$, $B_i^\pi(\varepsilon_{i,j})$ is a j-th energy Bayesian factor of the i-th ROI, and $\varepsilon_{i,j}$ is energy information of a current ray.

20. The electronic device according to claim 19, wherein after the determining an energy decision function based on the energy Bayesian factor, the method further comprises:
updating the energy prior probability using the energy decision function.

* * * * *